(12) United States Patent
Hinck et al.

(10) Patent No.: US 12,428,460 B2
(45) Date of Patent: *Sep. 30, 2025

(54) ENGINEERED TGF-BETA MONOMERS AND THEIR USE FOR INHIBITING TGF-BETA SIGNALING

(71) Applicants: University of Pittsburgh—Of the Commonwealth System of Higher Education, Pittsburgh, PA (US); National Research Council of Canada, Ottawa (CA)

(72) Inventors: Andrew Peterson Hinck, Pittsburgh, PA (US); Traian Sulea, Ottawa (CA)

(73) Assignees: University of Pittsburgh—Of the Commonwealth System of Higher Education, Pittsburgh, PA (US); National Research Council of Canada, Ottawa (CA)

( * ) Notice: Subject to any disclaimer, the term of this patent is extended or adjusted under 35 U.S.C. 154(b) by 422 days.

This patent is subject to a terminal disclaimer.

(21) Appl. No.: 17/369,736

(22) Filed: Jul. 7, 2021

(65) Prior Publication Data

US 2021/0332096 A1    Oct. 28, 2021

Related U.S. Application Data

(63) Continuation of application No. 16/461,747, filed as application No. PCT/US2017/062233 on Nov. 17, 2017, now Pat. No. 11,091,523.

(60) Provisional application No. 62/423,920, filed on Nov. 18, 2016.

(51) Int. Cl.
    C07K 14/495    (2006.01)
    A61K 38/00     (2006.01)

(52) U.S. Cl.
    CPC ............ *C07K 14/495* (2013.01); *A61K 38/00* (2013.01); *C07K 2319/00* (2013.01); *C07K 2319/30* (2013.01); *C07K 2319/31* (2013.01)

(58) Field of Classification Search
    None
    See application file for complete search history.

(56) References Cited

U.S. PATENT DOCUMENTS

| | | | |
|---|---|---|---|
| 5,595,756 A * | 1/1997 | Bally | A61K 9/1272 264/4.1 |
| 5,766,897 A * | 6/1998 | Braxton | C07K 1/1077 435/219 |
| 11,091,523 B2 * | 8/2021 | Hinck | A61K 45/06 |
| 2019/0359667 A1 | 11/2019 | Hinck et al. | |

FOREIGN PATENT DOCUMENTS

WO    WO 2011/094749    8/2011

OTHER PUBLICATIONS

Skolnick et al (Trends Biotechnol. Jan. 2000;18(1):34-9), (Year: 2000).*
Burgess et al. (J. Cell Biol. 111:2129-2138, 1990) (Year: 1990).*
Lazar et al. (Mol. Cell. Biol., 8:1247-1252, 1988) (Year: 1988).*
Miosge (Proc Natl Acad Sci U S A. Sep. 15, 2015;112(37):E5189-98) (Year: 2015).*
Bork (Genome Research, 2000,10:398-400) (Year: 2000).*
Haque et al (Human Vaccines & Immunotherapeutics; 2017, vol. 13, No. 8, 1741-1750) (Year: 2017).*
Sporn et al, "Chemoprevention of Cancer," Carcinogenesis, vol. 21 (2000), 525-530 (Year: 2000).*
Auerbach et al (Cancer and Metastasis Reviews, 2000, 19: 167-172) (Year: 2000).*
Gura T (Science, 1997, 278(5340): 1041-1042) (Year: 1997).*
Jain RK (Scientific American, Jul. 1994,58-65) (Year: 1994).*
Jonson et al (Protein Engineering vol. 14 No. 6 pp. 397-402, 2001) (Year: 2001).*
Amatayakul-Chantler et al., "[Ser$^{77}$] Transforming Growth Factor-β1. Selective Biological Activity and Receptor Binding in Mink Lung Epithelial Cells," *J. Biol. Chem.*, vol. 269:27687-27691, 1994.
Auerbach et al., "Angiogenesis assays: Problems and Pitfalls," *Cancer Metastasis Rev.*, vol. 19:167-172, 2000.
Baardsnes et al., "Tβ-II Discriminates the High- and Low-Affinity TGF-β Isoforms via Two Hydrogen-Bonded Ion Pairs," *Biochem.*, vol. 48:2146-2155, 2009.
Bork, "Powers and Pitfalls in Sequence Analysis: The 70% Hurdle," *Genome Res.*, vol. 10:398-400, 2000.
Bowie et al., "Deciphering the Message in Protein Sequences: Tolerance to Amino Acid Substitutions," *Science*, vol. 247:1306-1310, 1990.
Burgess et al., "Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue," *J. Cell Biol.*, vol. 111:2129-2138, 1990.
Burt, "Evolutionary Grouping of the Transforming Growth Factor-β Superfamily," *Biochem Biophys Res Commun* 184(2): 590-595, 1992.

(Continued)

*Primary Examiner* — Brian Gangle
*Assistant Examiner* — Andrea K McCollum
(74) *Attorney, Agent, or Firm* — Klarquist Sparkman, LLP

(57) ABSTRACT

Recombinant transforming growth factor (TGF)-β monomers modified to inhibit dimerization and block TGF-β signaling are described. The recombinant TGF-β monomers lack the ability to bind and recruit TGF-β type I receptor (TβRI), but retain the capacity to bind the high affinity TGF-β type II receptor (TβRII), and in some instances, include mutations that increase their affinity for TβRII. Nucleic acid molecules and vectors encoding the recombinant TGF-β monomers are also described. Isolated cells, such as T cells, can be re-programmed with a TGF-β monomer-encoding nucleic acid or vector to secrete the monomer. Use of the recombinant TGF-β monomers and/or cells producing the recombinant TGF-β monomers, to inhibit TGF-β signaling, such as to treat disorders associated with aberrant TGF-β signaling, are also described.

19 Claims, 20 Drawing Sheets

Specification includes a Sequence Listing.

(56) References Cited

OTHER PUBLICATIONS

De Crescenzo et al., "Three Key Residues Underlie the Differential Affinity of the TGFβ Isoforms for the TGFβ Type II Receptor," *J Mol Biol* 355: 47-62, 2006.
Gura, "Systems for Identifying New Drugs are Often Faulty," *Science*, vol. 278:1041-1042, 1997.
Haque et al., "Transforming Growth Factor-β: A Therapeutic Target for Cancer," *Hum. Vaccin. Immunother.*, vol. 13:1741-1750, 2017.
Huang et al., "Biological Activity Differences between TGF-β1 and TGF-β3 Correlate with Differences in the Rigidity and Arrangement of their Component Monomers," *Biochem.*, vol. 53:5737-5749, 2014.
International Search Report and Written Opinion of PCT/US2017/062233, dated Feb. 26, 2018, 12 pages.
Jain, "Barriers to Drug Delivery in Solid Tumors," *Sci. Am.*, pp. 58-65, 1994.
Kim et al., "An Engineered Transforming Growth Factor β (TGF-β) Monomer that Functions as a Dominant Negative to Block TGF-β Signaling," *J. Biol. Chem.*, vol. 292:7173-7188, 2017.
Lazar et al., "Transforming Growth Factor a: Mutation of Aspartic Acid 47 and Leucine 48 Results in Different Biological Activities," *Mol. Cell Biol.*, vol. 8:1247-1252, 1988.
Lonning et al., "Antibody Targeting of TGF-β in Cancer Patients," *Curr. Pharm. Biotechnol.*, vol. 12:2176-2189, 2011.
Massagué, "The Transforming Growth Factor-β Family," *Annu Rev Cell Biol* 6: 597-641, 1990.
Sporn et al., "Chemoprevention of Cancer," *Carcinogenesis*, vol. 21:525-530, 2000.
Yingling et al., "Development of TGF-β Signalling Inhibitors for Cancer Therapy," *Nature Rev.*, vol. 3:1011-1022, 2004.
Zúñiga et al., "Assembly of TβRI:TβRII:TGFβ Ternary Complex in vitro with Receptor Extracellular Domains is Cooperative and Isoform-dependent," *J. Biol. Med.*, vol. 354:1052-1068, 2005.

\* cited by examiner

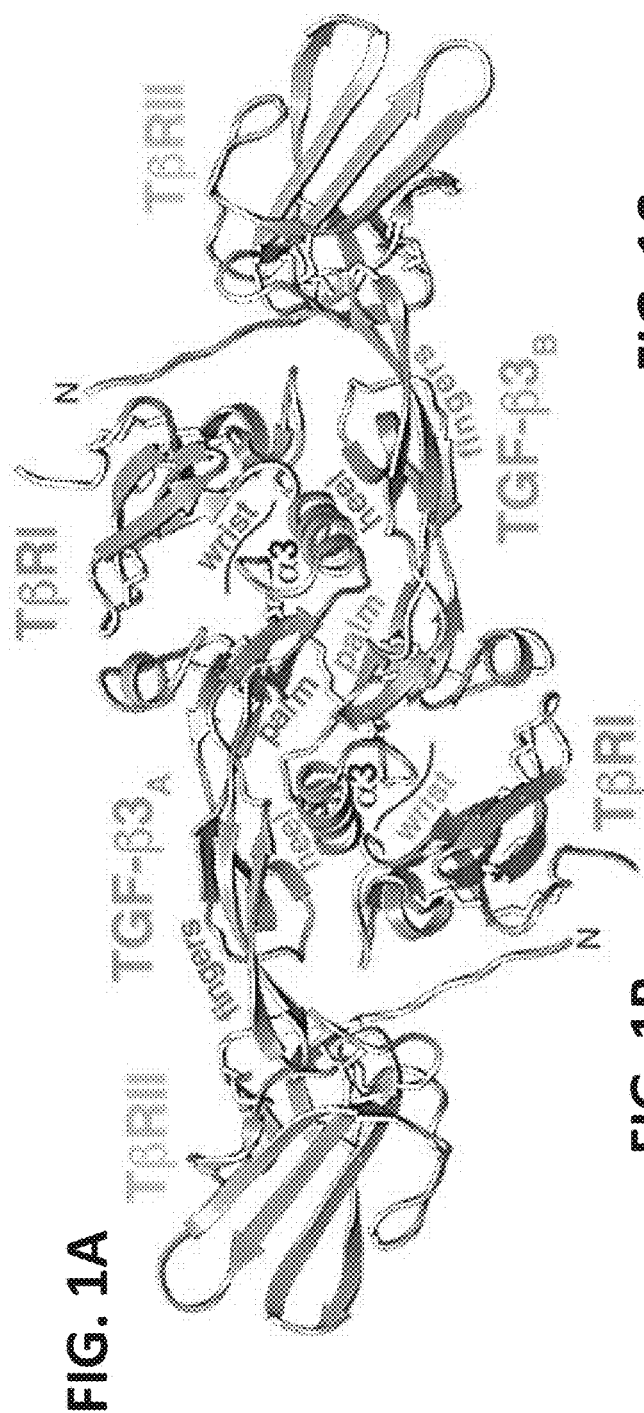
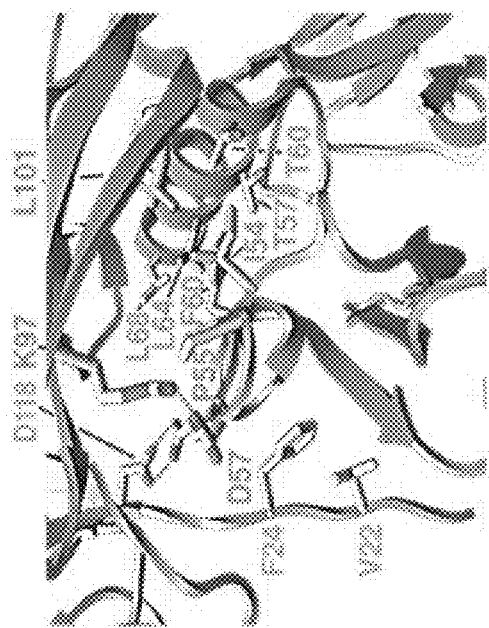
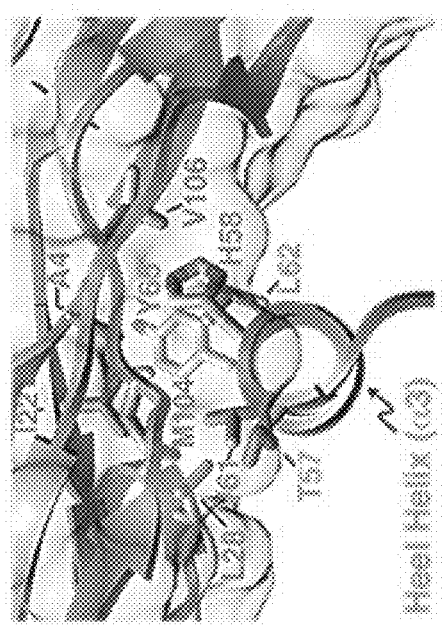
FIG. 1A
FIG. 1B
FIG. 1C

FIG. 1D

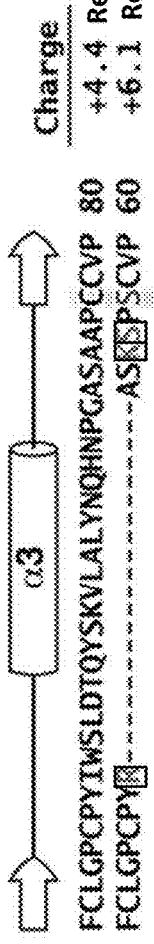

|  |  |  | α3 |  |  | Charge |  |
|---|---|---|---|---|---|---|---|
| TGF-β1 | 43 | FCLGPCPYIWSLDTQYSKVLALYNQHNPGASAAPCCVP | 80 | +4.4 | Residues 43-80 of SEQ ID NO: 1 |
| mmTGF-β1 | 43 | FCLGPCPY--------------------AS[ ]PSCVP | 60 | +6.1 | Residues 43-60 of SEQ ID NO: 7 |
| TGF-β2 | 43 | FCAGACPYLWSSDTQHTKVLSLYNTINPEASASPCCVS | 80 | +1.1 | Residues 43-80 of SEQ ID NO: 2 |
| mTGF-β2 | 43 | FCAGACPYLWSSDTQHTKVLSLYNTINPEASASPCCVS | 80 | +1.1 | Residues 43-80 of SEQ ID NO: 5 |
| mmTGF-β2 | 43 | FCAGACPY[ ]--------------------AS[ ]PSCVS | 60 | +3.9 | Residues 43-60 of SEQ ID NO: 8 |
| TGF-β3 | 43 | FCSGPCPYLRSADTTHSTVLGLYNTLNPEASASPCCVP | 80 | -0.9 | Residues 43-80 of SEQ ID NO: 3 |
| mmTGF-β3 | 43 | FCSGPCPYLRSADTTHSTVLGLYNTLNPEASASPSCVP | 80 | -0.9 | Residues 43-80 of SEQ ID NO: 6 |
| mmTGF-β3 | 43 | FCSGPCPY[ ]--------------------[ ]SPSCVP | 60 | -3.1 | Residues 43-60 of SEQ ID NO: 9 |

FIG. 1E

| Residues | SEQ ID NO: |  | 25 | 92 94 |  |
|---|---|---|---|---|---|
| 23-36 | TGF-β1 | 1 | 23 DFRKDLGWKWIHEP 36 |  |  |
| 22-36 | TGF-β3 | 3 | 23 DFRQDLGWKWIHEP 36 |  |  |
| 23-36 | TGF-β2 | 2 | 23 DFKRDLGWKWIHEP 36 |  |  |
| 23-36 | mmTGF-β2 | 8 | 23 DFKRDLGWKWIHEP 36 |  |  |
| 23-36 | mmTGF-β2-7m | 10 | 23 DF[ ]DLGWKWIHEP 36 |  |  |
| 88-100 | TGF-β1 | 1 | 93 IVYYVGRKPKVEQ 100 |  |  |
| 88-100 | TGF-β3 | 3 | 93 ILYYVGRTPKVEQ 100 |  |  |
| 88-100 | TGF-β2 | 2 | 93 ILYIGNTPKIEQ 100 |  |  |
| 68-80 | mmTGF-β2 | 8 | 93 ILYIGNTPKIEQ 100 |  |  |
| 68-80 | mmTGF-β2-7m | 10 | 93 I[ ]Y[ ][ ]P[ ]EQ 100 |  |  |

FIG. 1F

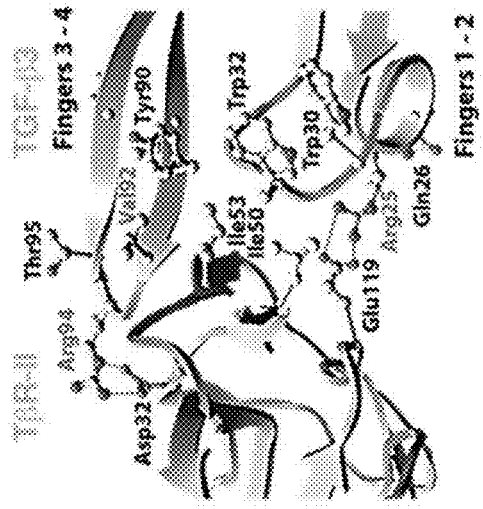

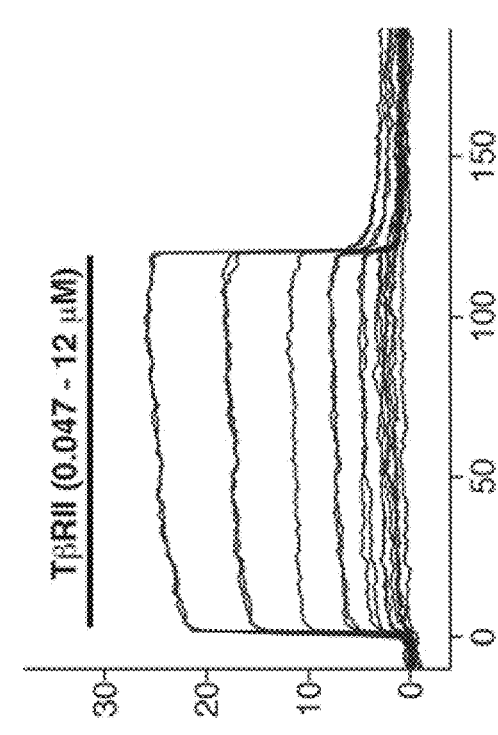
FIG. 3A TGF-β2
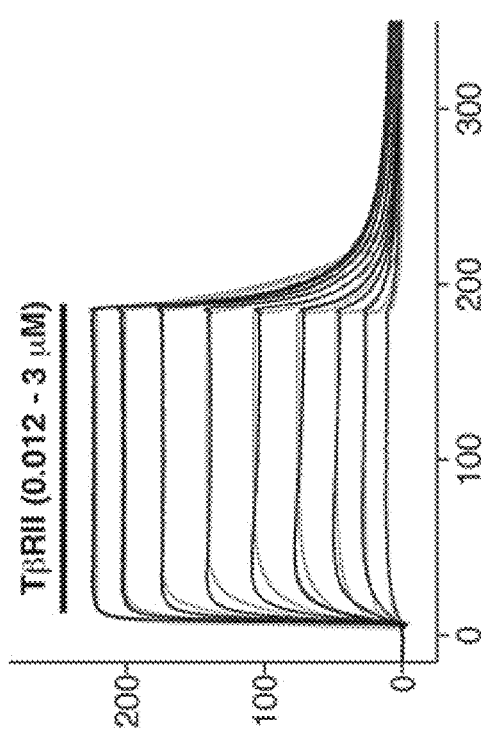
FIG. 3B mmTGF-β2
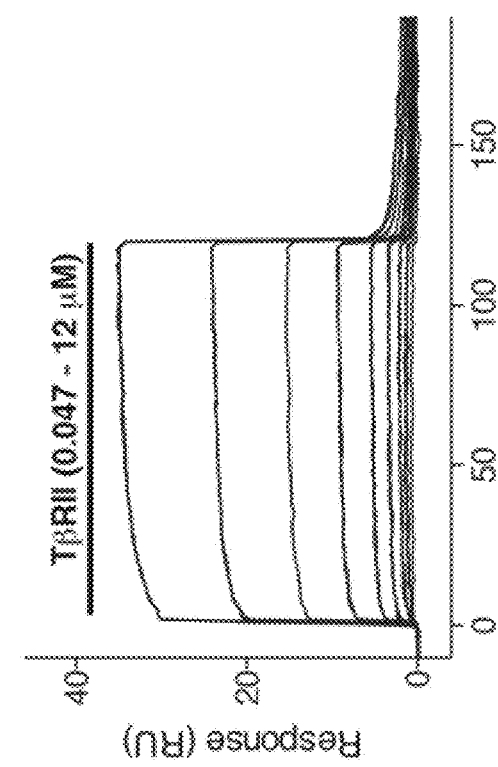
FIG. 3C TGF-β3
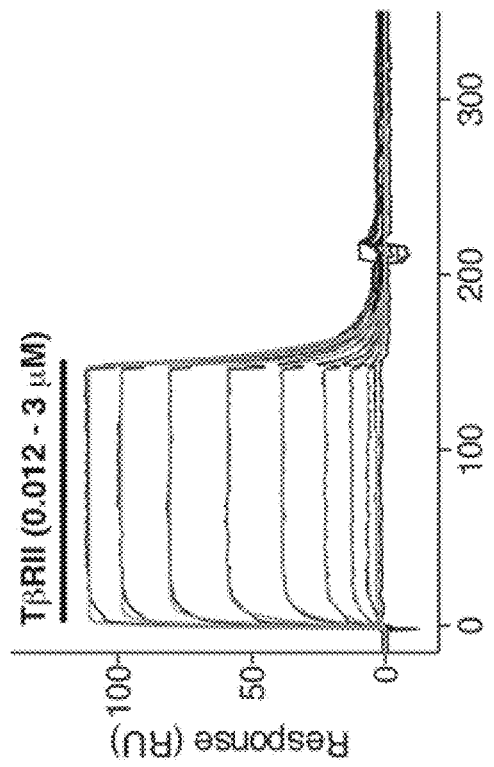
FIG. 3D mmTGF-β2-7M

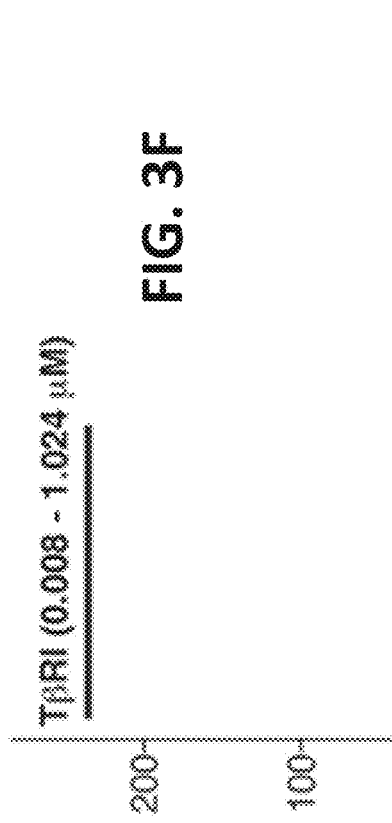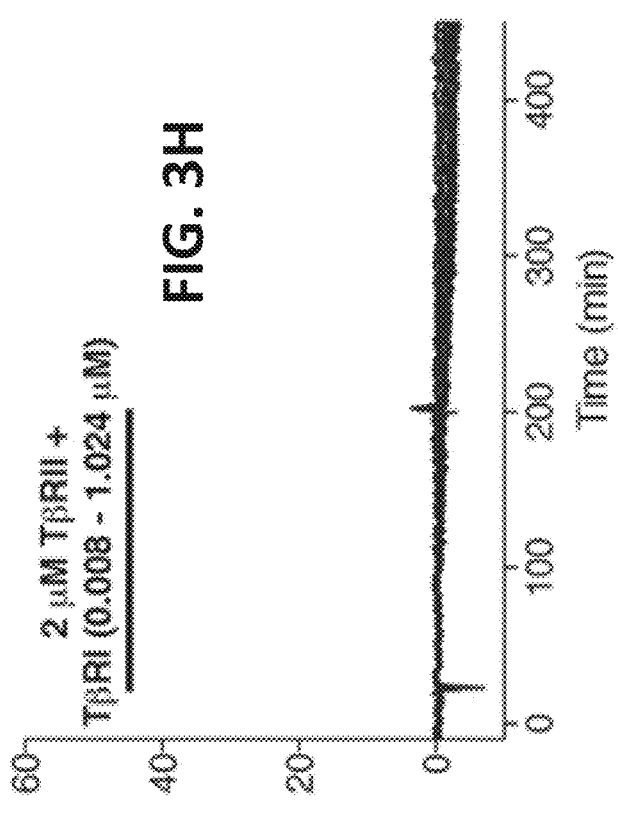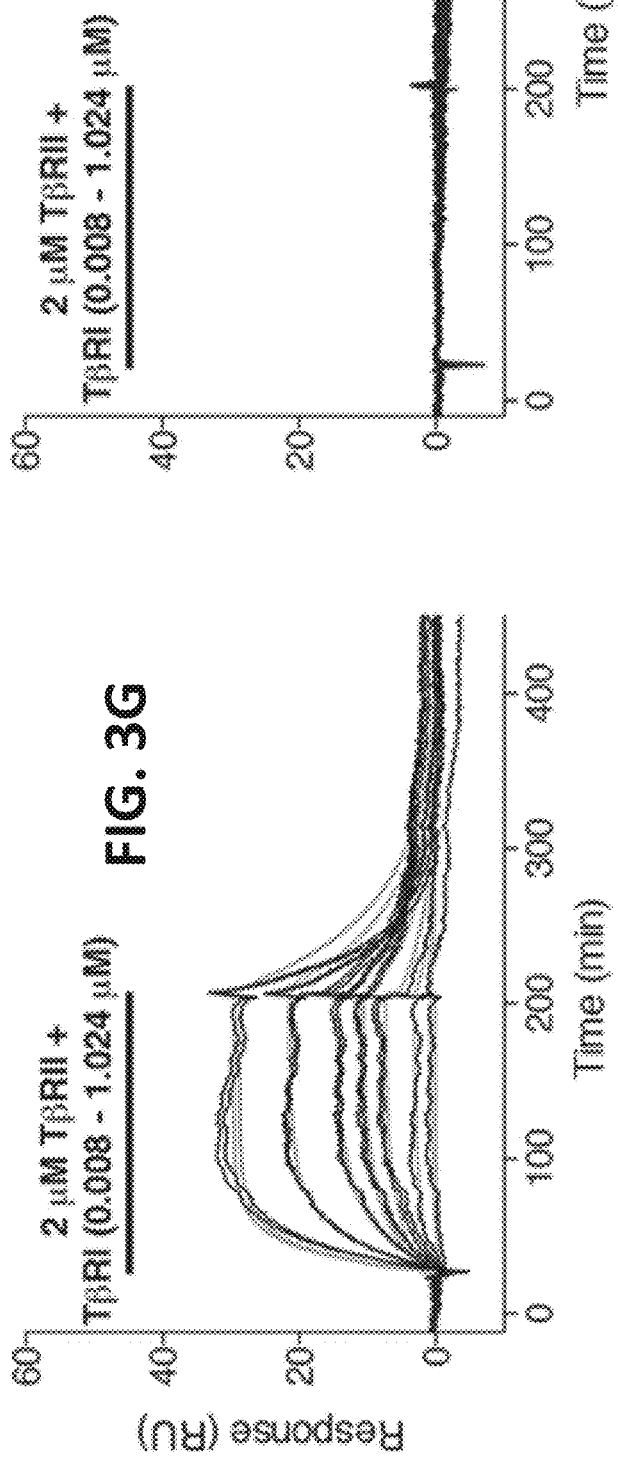

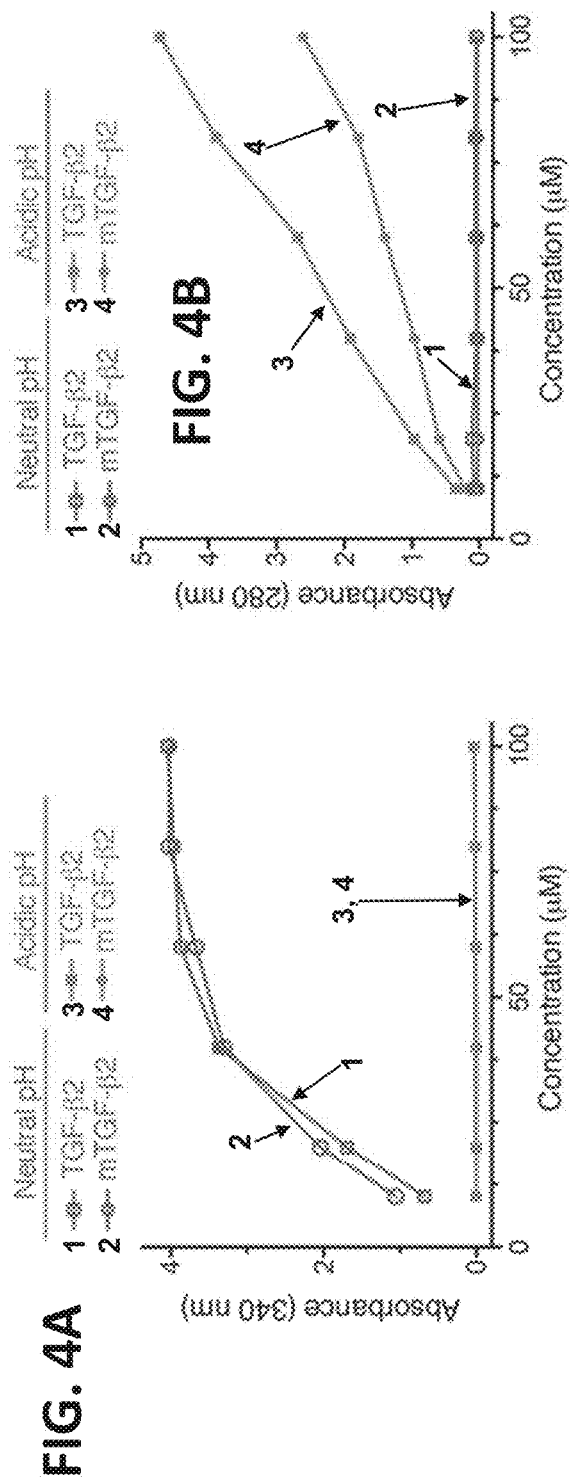
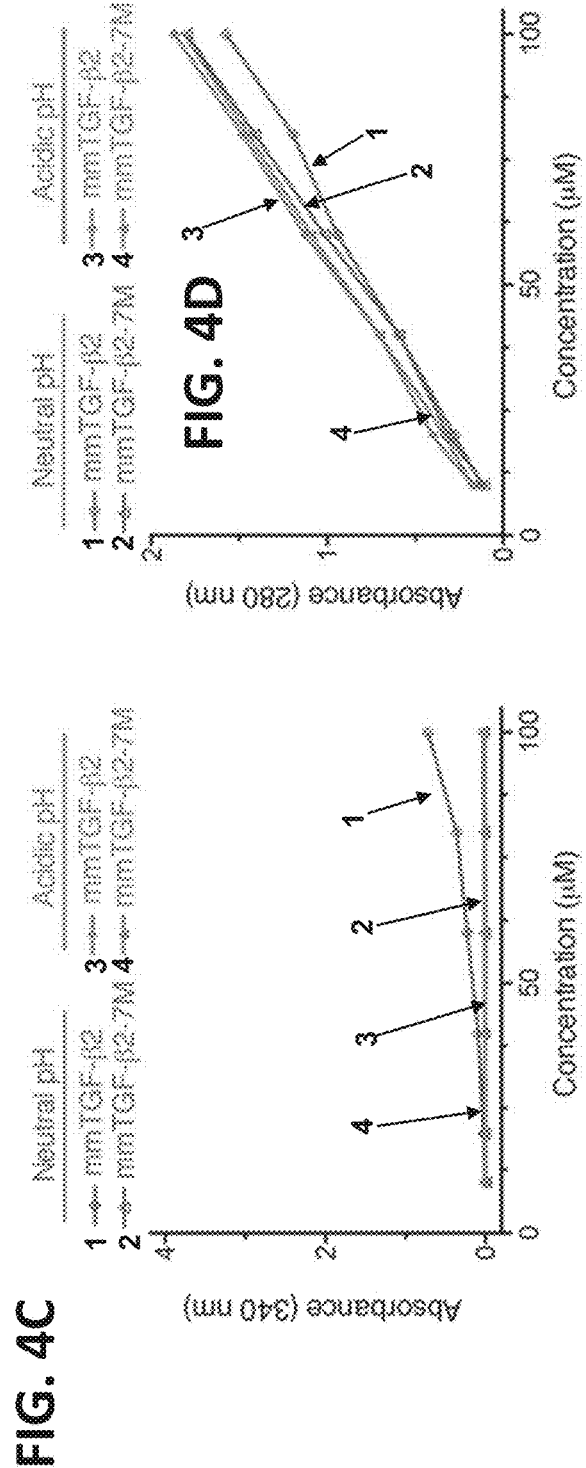
FIG. 4A
FIG. 4B
FIG. 4C
FIG. 4D

FIG. 8

```
---------- --------AL DTNYCFSSTE KNCCVRQLYI DFRKDLGWKW   32  TGF-β1
---------- --------AL DTNYCFSSTE KNCCVRQLYI DFRKDLGWKW   32  mmTGF-β1
---------- --------AL DAAYCFRNVQ DNCCLRPLYI DFKRDLGWKW   32  TGF-β2
---------- --------AL DAAYCFRNVQ DNCCLRPLYI DFKRDLGWKW   32  mTGF-β2
---------- --------AL DAAYCFRNVQ DNCCLRPLYI DFKRDLGWKW   32  mmTGF-β2
---------- --------AL DAAYCFRNVQ DNCCLRPLYI DFKRDLGWKW   32  mmTGF-β2-7M
-GLNDIFEAQ KIEWHEEFAL DAAYCFRNVQ DNCCLRPLYI DFKRDLGWKW   49  avi-mmTGF-β2-7M
---------- --------AL DTNYCFRNLE ENCCVRPLYI DFRQDLGWKW   32  TGF-β3
---------- --------AL DTNYCFRNLE ENCCVRPLYI DFRQDLGWKW   32  mTGF-β3
-GLNDIFEAQ KIEWHEEFAL DTNYCFRNLE ENCCVRPLYI DFRQDLGWKW   49  avi-TGF-β3
---------- --------AL DTNYCFRNLE ENCCVRPLYI DFRQDLGWKW   32  mmTGF-β3

IHEPKGYHAN FCLGPCPYIW SLDTQYSKVL ALYNQHNPGA SAAPCCVPQA   82  TGF-β1
IHEPKGYHAN FCLGPCPY-- ---------- --------RA SKSPSCVPQA   62  mmTGF-β1
IHEPKGYNAN FCAGACPYLW SSDTQHSKVL SLYNTINPEA SASPCCVSQD   82  TGF-β2
IHEPKGYNAN FCAGACPYLW SSDTQHSKVL SLYNTINPEA SASPSCVSQD   82  mTGF-β2
IHEPKGYNAN FCAGACPY-- ---------- --------RA SKSPSCVSQD   62  mmTGF-β2
IHEPKGYNAN FCAGACPY-- ---------- --------RA SKSPSCVSQD   62  mmTGF-β2-7M
IHEPKGYNAN FCAGACPY-- ---------- --------RA SKSPSCVSQD   79  avi-mmTGF-β2-7M
VHEPKGYYAN FCSGPCPYLR SADTTHSTVL GLYNTLNPEA SASPCCVPQD   82  TGF-β3
VHEPKGYYAN FCSGPCPYLR SADTTHSTVL GLYNTLNPEA SASPSCVPQD   82  mTGF-β3
VHEPKGYYAN FCSGPCPYLR SADTTHSTVL GLYNTLNPEA SASPCCVPQD   99  avi-TGF-β3
VHEPKGYYAN FCSGPCPY-- ---------- -------EE SDSPSCVPQD   62  mmTGF-β3

LEPLPIVYYV GRKPKVEQLS NMIVRSCKCS   (SEQ ID NO: 1)  112  TGF-β1
LEPLPIVYYV GRKPKVEQLS NMIVRSCKCS   (SEQ ID NO: 7)   92  mmTGF-β1
LEPLTILYYI GKTPKIEQLS NMIVKSCKCS   (SEQ ID NO: 2)  112  TGF-β2
LEPLTILYYI GKTPKIEQLS NMIVKSCKCS   (SEQ ID NO: 5)  112  mTGF-β2
LEPLTILYYI GKTPKIEQLS NMIVKSCKCS   (SEQ ID NO: 8)   92  mmTGF-β2
LEPLTIVYYV GRKPKVEQLS NMIVKSCKCS   (SEQ ID NO: 10)  92  mmTGF-β2-7M
LEPLTIVYYV GRKPKVEQLS NMIVKSCKCS   (SEQ ID NO: 11) 109  avi-mmTGF-β2-7M
LEPLTILYYV GRTPKVEQLS NMVVKSCKCS   (SEQ ID NO: 3)  112  TGF-β3
LEPLTILYYV GRTPKVEQLS NMVVKSCKCS   (SEQ ID NO: 6)  112  mTGF-β3
LEPLTILYYV GRTPKVEQLS NMVVKSCKCS   (SEQ ID NO: 4)  129  avi-TGF-β3
LEPLTILYYV GRTPKVEQLS NMVVKSCKCS   (SEQ ID NO: 9)   92  mmTGF-β3
```

ENGINEERED TGF-BETA MONOMERS AND THEIR USE FOR INHIBITING TGF-BETA SIGNALING

CROSS REFERENCE TO RELATED APPLICATIONS

This application is the continuation of U.S. patent application Ser. No. 16/461,747, filed May 16, 2019, issued as U.S. Pat. No. 11,091,523 on Aug. 17, 2021, which is the U.S. National Stage of International Application No. PCT/US2017/062233, filed Nov. 17, 2017, published in English under PCT Article 21 (2), which claims the benefit of U.S. Provisional Application No. 62/423,920, filed Nov. 18, 2016. The above-listed applications are herein incorporated by reference in their entirety.

ACKNOWLEDGMENT OF GOVERNMENT SUPPORT

This invention was made with government support under grant number GM058670, awarded by the National Institutes of Health. The government has certain rights in the invention.

FIELD

This disclosure concerns recombinant transforming growth factor (TGF)-β monomers modified to inhibit dimerization while retaining the capacity to bind the high affinity TGF-β type II receptor (TβRII). This disclosure further concerns use of the recombinant TGF-β monomers to inhibit TGF-β signaling.

BACKGROUND

TGF-β is a multifunctional cytokine with diverse biological effects on cellular processes, including cell proliferation, migration, differentiation, and apoptosis. The three mammalian TGF-β isoforms, TGF-β1, -β2 and -β3, exert their functions through a cell surface receptor complex composed of type I (TβRI) and type II (TβRII) serine/threonine kinase receptors. Receptor activation induces both SMAD proteins and other downstream targets, including Ras, RhoA, TAK1, MEKK1, PI3K, and PP2A, to produce the full spectrum of TGF-β responses (Roberts and Wakefield, *Proc Natl Acad Sci USA* 100:8621-8623, 2003; Derynck and Zhang, *Nature* 425:577-584, 2003; Massagué, *Cell* 134:215-230, 2008).

TGF-β proteins are known to promote the progression of fibrotic disorders and certain types of cancer. In the context of fibrotic disorders, TGF-β potently stimulates the expression of extracellular matrix (ECM) proteins. Dysregulation of the ECM remodeling can lead to pathological fibrosis. The role of TGF-β in cancer is multi-faceted. TGF-β isoforms, TGF-β1, -β2 and -β3 are also known to suppress host immune surveillance and to stimulate epithelial-to-mesenchymal transitions, which drive cancer progression and metastasis.

SUMMARY

Described herein are engineered TGF-β monomers that are capable of blocking TGF-β signaling. The engineered monomers inhibit TGF-β signaling by preventing TGF-β dimerization and recruitment of TβRI.

Provided herein is a recombinant TGF-β monomer that includes a cysteine to serine substitution at amino acid residue 77; a deletion of amino acid residues 52-71; and at least one amino acid substitution that increases the net charge of the monomer. In some embodiments, the TGF-β monomer further includes at least one amino acid substitution that increases affinity of the TGF-β monomer for TGF-β type II receptor (TβRII). The TGF-β monomer can be, for example, a TGF-β2, TGF-β1 or TGF-β3 monomer, such as a human, rat, mouse or other mammalian TGF-β2, TGF-β1 or TGF-β3 monomer.

Fusion proteins that include a TGF-β monomer and a heterologous protein are also provided. Further provided are compositions that include a recombinant TGF-β monomer or fusion protein disclosed herein and a pharmaceutically acceptable carrier, diluent, or excipient.

Further provided are methods of inhibiting TGF-β signaling in a cell by contacting the cell with a recombinant TGF-β monomer, fusion protein or composition disclosed herein. In some embodiments, the method is an in vitro method. In other embodiments, the method is an in vivo method that includes administering the recombinant TGF-β monomer, fusion protein or composition to a subject having a disease or disorder associated with aberrant TGF-β signaling.

Also provided are nucleic acid molecules and vectors that encode a recombinant TGF-β monomer disclosed herein. Further provided are isolated cells, such as isolated T lymphocytes, that comprise the recombinant TGF-β monomer-encoding nucleic acid molecule or vector.

Methods of treating a disease or disorder associated with aberrant TGF-β signaling in a subject by administering to the subject an isolated cell (such as a T cell) comprising the disclosed nucleic acids or vectors are further provided.

The foregoing and other objects, features, and advantages of the invention will become more apparent from the following detailed description, which proceeds with reference to the accompanying figures.

BRIEF DESCRIPTION OF THE DRAWINGS

FIGS. 1A-1F: Structure of the TGF-β signaling complex and sequences of the engineered TGF-β variants lacking the interfacial α-helix. (FIG. 1A) Cartoon representation of the TGF-β signaling complex formed between the human TGF-β3 homodimer and the extracellular ligand binding domains of the human TGF-β type I and type II receptors, TβRI and TβRII (PDB 2PJY) (Groppe et al., *Mol Cell* 29, 157-168, 2008). The disulfide bonds, including the single inter-chain disulfide connecting the TGF-β monomers, are shown. The TGF-β monomers are described as curled left hands, with the heel formed by a 3-1/2 turn α-helix (α3) and the four fingers formed by the β-strands that extend from the cystine knot that stabilizes each monomer. (FIG. 1B) Expanded view illustrating packing interactions formed by hydrophobic residues that emanate from the heel α-helix of one TGF-β3 monomer with hydrophobic residues from the palm region of the opposing TGF-β3 monomer. (FIG. 1C) Expanded view illustrating ionic, hydrogen bonding, and hydrophobic interactions that stabilize TβRI at the composite interface formed by both monomers of TGF-β3 and TβRII. (FIG. 1D) Sequence alignment of TGF-β1, β2, and -β3 with monomeric variants in which Cys77, which normally forms the inter-chain disulfide bond, is substituted with serine (mTGF-β2 and mTGF-β3) or mini monomeric variants in which Cys77 is substituted with serine, residues 52-71 have been deleted, and 2 or 3 additional residues have been substituted (mmTGF-β1, mmTGF-β2, and mmTGF-β3). Calculated net charge of the corresponding monomers at pH 7.0 is shown on the right. (FIG. 1E) Sequence alignment of TGF-β1, -β3, -β2, mmTGF-β2, and mmTGF-β2-7M in the TβRII binding region. Residues in the TβRII binding interface are indicated by shading. Residues substituted in mmTGF-β2-7M relative to mmTGF-β2 are indicated by boxes, and include K25R, I92V, and N94R, which were shown previously to be necessary and sufficient for high affinity TβRII binding (Baardsnes et al., *Biochemistry* 48:2146-2155, 2009; De Crescenzo et al., *J Mol Biol* 355: 47-62, 2006). (FIG. 1F) Interface between TGF-β3 and TβRII.

FIGS. 2A-2D: Structure of mmTGF-β2. (FIG. 2A) Assigned $^{1}H-^{15}N$ HSQC spectrum of mmTGF-β2 recorded in 10 mM sodium phosphate, 10 mM CHAPS, 5% $2H_2O$, pH 4.70, 37° C., 800 MHz. Assigned backbone amide signals are indicated by their residue number and one letter amino acid code. (FIG. 2B) Overlay of 1.8 Å crystal structure of mmTGF-β2 with one of the monomers from the 1.8 Å crystal structure of TGF-β2 (PDB 2TGI). Major structural features are indicated, along with the engineered loop in mmTGF-β2 which takes the place of the palm (α3) helix in TGF-β2. (FIG. 2C) Overlay of the two mmTGF-β2 chains (Chain A and B) from the crystallographic asymmetric unit. Other details as in FIG. 2B. (FIG. 2D) Overlay of mmTGF-β2 and TGF-β2 as in FIG. 2B, but with the aligned positions restricted to the residues 18-45 and 61-87 in fingers 1/2 and 3/4, respectively.

FIGS. 3A-3H: Binding properties of mmTGF-β2 and mmTGF-β2-7M. (FIGS. 3A and 3B) Surface plasmon resonance (SPR) sensorgrams for injection of a two-fold dilution series from 0.047-12 μM of TβRII over immobilized TGF-β2 (FIG. 3A) or mmTGF-β2 (FIG. 3B). (FIGS. 3C-3H) SPR sensorgrams for injection of a two-fold dilution series from 0.012-3 μM of TμII (FIGS. 3C and 3D), 0.008-1.024 μM of TβRI (FIGS. 3E and 3F), or 0.008-1.024 μM TβRII in the presence of 2 μM TβRII in both the running buffer and injected samples (FIGS. 3G and 3H) over immobilized avi-TGF-β3 (FIGS. 3C, 3E and 3G) or avi-mmTGF-β2-7M (FIGS. 3D, 3F and 3H). Sensorgrams shown in FIGS. 3C, 3D, and 3G were fitted to a 1:1 binding model; raw data and the fitted curve are shown. TGF-β2 and mmTGF-β2 were immobilized by direct carboiimide-based amine coupling to the sensor surface, while avi-TGF-β3 or avi-mmTGF-β2-7M were immobilized by capturing the enzymatically biotinylated proteins onto the surface of sensor chip coated streptavidin at high (ca. 8000 response unit (RU)) density.

FIGS. 4A-4D: Solubility of TGF-β2 and monomeric variants. (FIGS. 4A and 4C) TGF-β2 and mTGF-β2 (FIG. 4A), and mmTGF-β2 and mmTGF-β2-7M (FIG. 4C), were diluted from a concentrated stock in 100 mM acetic acid into either PBS at 7.4 (Neutral pH) or 100 mM acetic acid (Acidic pH) and the light scattering at 340 nm was measured. (FIGS. 4B and 4D) TGF-β2 and mTGF-β2 (FIG. 4B), and mmTGF-β2 and mmTGF-β2-7M (FIG. 4D) samples diluted into either PBS or 100 mM acetic acid were centrifuged for 5 minutes at 20,000× g and the protein absorbance at 280 nm was measured.

FIGS. 5A-5E: Structure of mmTGF-β2-7M and mmTGF-β2-7M:TβRII complex. (FIG. 5A) Assigned $^{1}H-^{15}N$ HSQC spectrum of mmTGF-β2-7M recorded in 10 mM sodium phosphate, 10 mM CHAPS, 5% $2H_2O$, pH 4.70, 37° C., 800 MHz. Assigned backbone amide signals are indicated by their residue number and one letter amino acid code. (FIG. 5B) Overlay of 1.8 Å crystal structure of mmTGF-β2-7M with one of the monomers from the 1.8 Å crystal structure of TGF-β2 (PDB 2TGI). Major structural features are indicated, along with the engineered loop in mmTGF-β2 which takes the place of the palm (α3) helix in TGF-β2. (FIG. 5C) Overlay of the three mmTGF-β2-7M chains (Chain A, B, and C) from the crystallographic asymmetric unit. Dashed line corresponds to missing segment in the region of the engineered loop in Chain C due to weak electron density. Other details as in FIG. 5B. (FIG. 5D) Overlay of the 1.8 Å crystal structure of mmTGF-β2-7M:TβRII complex with one of the TGF-β3 monomers and its bound TβRII from the 3.0 Å crystal structure of the TGF-β3:TβRII-TβRI complex (PDB 2PJY, TGF-β3 monomer and TβRII; TβRI not shown for clarity). Engineered loop in mmTGF-β2 which takes the place of the palm (α3) helix in TGF-β2 is depicted. (FIG. 5E) Overlay as in FIG. 5B, but expanded to show the near identity of critical hydrophobic and hydrogen-bonding/electrostatic interactions shown previously to be essential for high affinity TGF-β3:TβRII binding.

FIGS. 6A-6B: Signaling activity of TGF-β1 and variants. (FIG. 6A) TGF-β luciferase reporter activity for TGF-β1, mTGF-β3, and mmTGF-β2-7M shown in solid circles, squares, and triangles, respectively. The solid lines correspond to the fitted curves to derive the $EC_{50}$ (mmTGF-β2-7M was not fit due to the lack of signaling activity for this variant). (FIG. 6B) TGF-β luciferase reporter activity for cells treated with a sub-saturating concentration of TGF-β1 (8 pM) with increasing concentration of the indicated monomeric TGF-β variant added (mTGF-β3 and mmTGF-β2-7M shown in open squares and closed triangles, respectively). The solid lines correspond to the fitted curves for mTGF-β3 to derive the $EC_{50}$ and to the fitted curve for mTGF-β2-7M to derive the $IC_{50}$.

FIGS. 7A-7B: Time-resolved fluorescence resonance energy transfer (TR-FRET) assay for ligand-mediated assembly of a TβRI:TβRII complexes. (FIG. 7A) Structure of the TGF-β3:TβRII-TβRI complex with C-terminal tags and fluorescently labeled donor and acceptor proteins that associate with the tags. TβRII has a C-terminal hexahistidine tag ($His_6$) and is bound by a $Tb^{3+}$-cryptate labeled anti-hexahistidine tag antibody (Cisbio, Bedford, MA). TβRI has a C-terminal biotinylated avitag and is bound by $XL_{665}$-labeled streptavidin (Cisbio, Bedford, MA). The single lysine residue in TβRI C-terminal avitag that is biotinylated is labeled as "K-B". (FIG. 7B) TR-FRET ΔF values for samples consisting of the indicated components added—in all cases the buffer consisted of 25 mM Tris, 50 mM NaCl, pH 7.4 with 2 nM $Tb^{3+}$-cryptate labeled anti-hexahistidine tag antibody and 30 nM $XL_{665}$-labeled streptavidin. TR-FRET ΔF corresponds to ratio of the acceptor ($XL_{665}$) emission at 665 nm relative to the donor ($Tb^{3+}$-cryptate) emission at 490 nm.

FIG. 8: Alignment of the amino acid sequences of the TGF-βs used in this study. Sequences are numbered on the figure such that the first residue following the N-terminal methionine is residue 1.

FIGS. 9A-9B: Secondary structure probabilities and backbone $^{15}N$ $T_2$ relaxation times for mmTGF-β2. (FIG. 9A) Secondary structure probabilities were calculated based on the backbone $H^N$, $N^H$, Cα, and $C^O$ and sidechain Cβ atoms using the program PECAN. β-strand and α-helix probabilities are plotted as positive and negative values, respectively. (FIG. 9B) $^{15}N$ $T_2$ relaxation times plotted as a function of residue number. Secondary structures shown above each graph correspond to those from the crystal structure of TGF-β2 (PDB 2TGI).

FIGS. 10A-10B: Secondary structure probabilities and backbone $^{15}N$ $T_2$ relaxation times for mmTGF-β2-7M. (FIG. 10A) Secondary structure probabilities were calculated based on the backbone $H^N$, $N^H$, Cα, and $C^O$ and sidechain Cβ atoms using the program PECAN. β-strand and α-helix probabilities are plotted as positive and negative values, respectively.

FIG. 15A) or TGF-β3 (10 pM; FIG. 15B) and increasing concentrations of mmTGF-β2-7M. Solid lines correspond to the fitted curve to derive the IC$_{50}$.

SEQUENCE LISTING

Figure 2A:
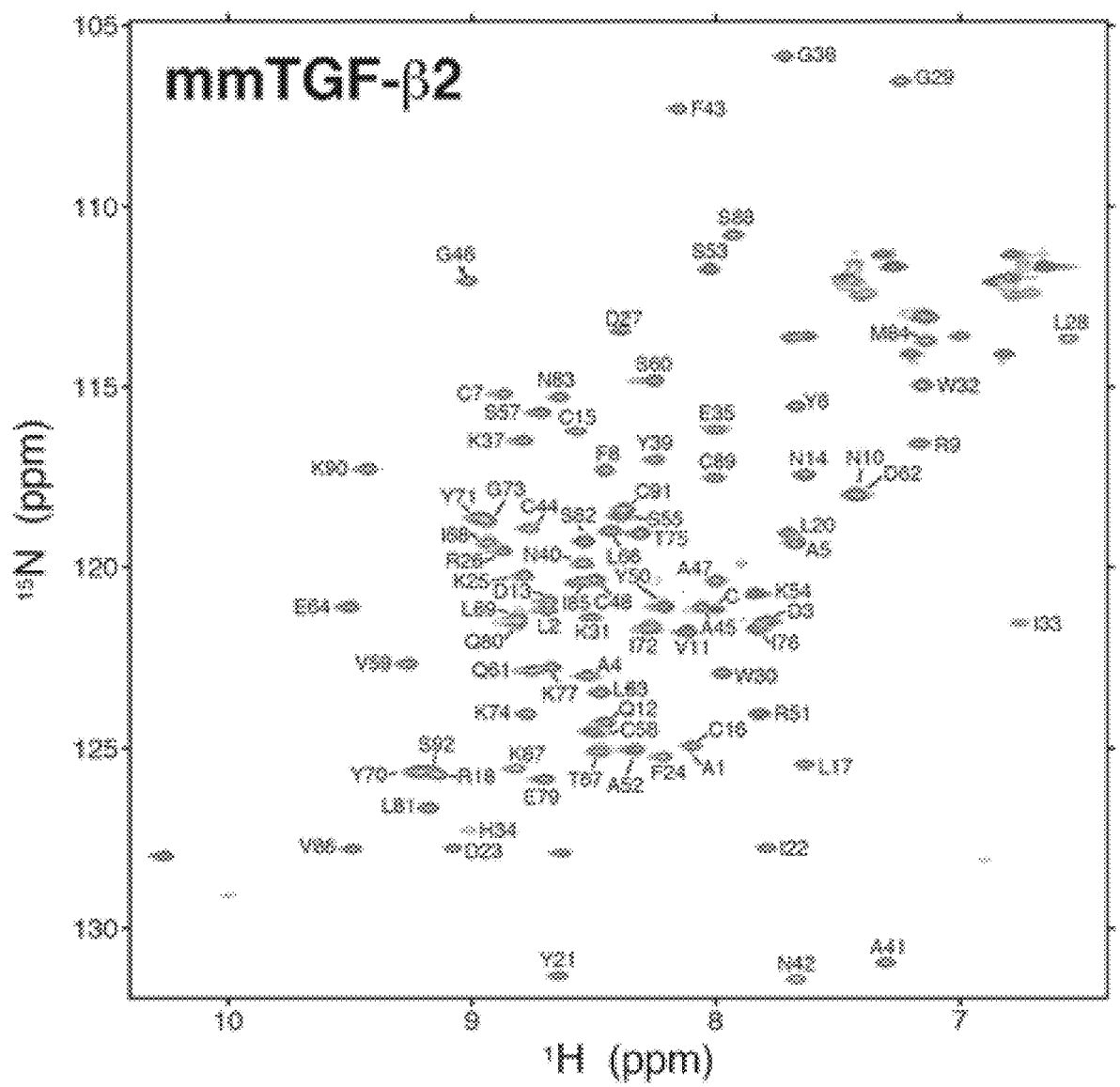
Figure 2B:
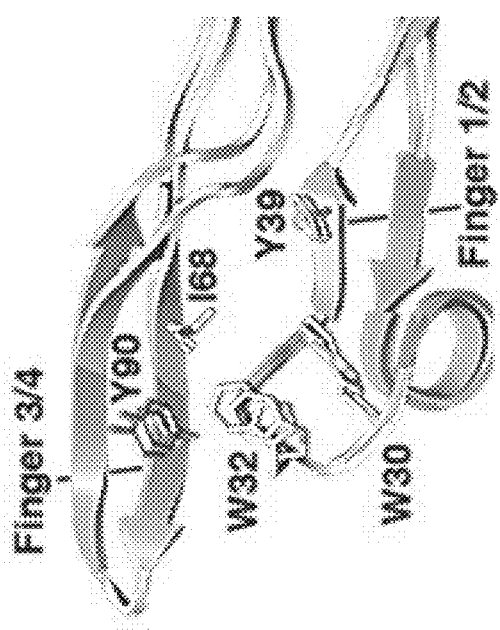
Figure 2C:
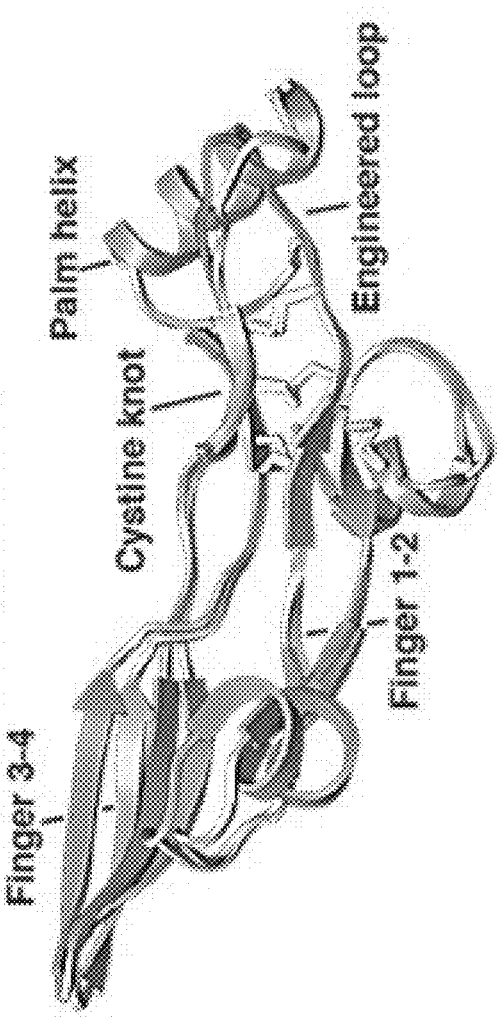
Figure 2D:
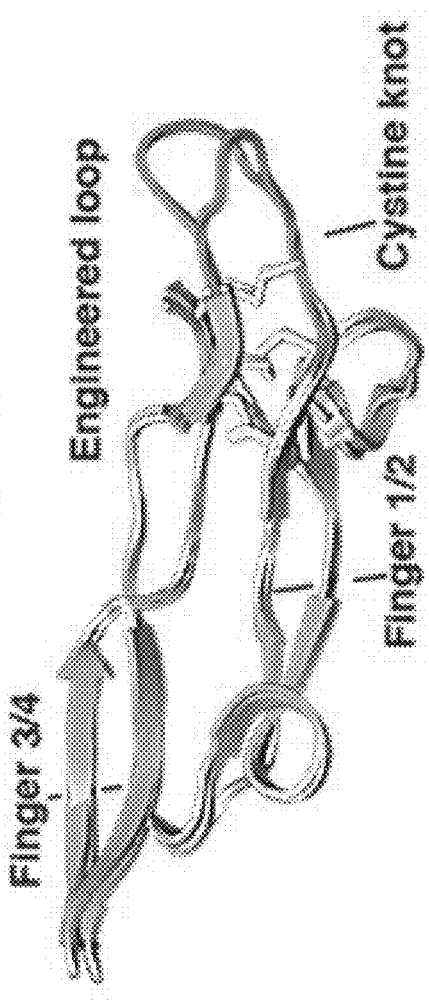

The amino acid sequences listed in the accompanying sequence listing are shown using standard three letter code for amino acids, as defined in 37 C.F.R. 1.822. The Sequence Listing is submitted as an ASCII text file, named 98053-08_ST25.txt, created on Jun. 1, 2023, 11,579 bytes, which is incorporated by reference herein. In the accompanying sequence listing:

SEQ ID NO: 1 is the amino acid sequence of wild-type human TGF-β1.

SEQ ID NO: 2 is the amino acid sequence of wild-type human TGF-β2.

SEQ ID NO: 3 is the amino acid sequence of wild-type human TGF-β3.

SEQ ID NO: 4 is the amino acid sequence of human TGF-β3 with an N-terminal Avitag.

SEQ ID NO: 5 is the amino acid sequence of an engineered human TGF-β2 monomer designated mTGF-β2.

SEQ ID NO: 6 is the amino acid sequence of an engineered human TGF-β3 monomer designated mTGF-β3.

SEQ ID NO: 7 is the amino acid sequence of an engineered human TGF-β1 monomer designated mmTGF-β1.

SEQ ID NO: 8 is the amino acid sequence of an engineered human TGF-β2 monomer designated mmTGF-β2.

SEQ ID NO: 9 is the amino acid sequence of an engineered human TGF-β3 monomer designated mmTGF-β3.

SEQ ID NO: 10 is the amino acid sequence of an engineered human TGF-β2 monomer designated mmTGF-β2-7M.

SEQ ID NO: 11 is the amino acid sequence of mmTGF-β2-7M with an N-terminal Avitag.

DETAILED DESCRIPTION

I. Abbreviations

AUC analytical ultracentrifugation
BSA bovine serum albumin
EC$_{50}$ effective concentration 50
FBS fetal bovine serum
IC$_{50}$ inhibitory concentration 50
NMR nuclear magnetic resonance
RU resonance unit
SPR surface plasmon resonance
TβRI transforming growth factor-β type I receptor
TβRII transforming growth factor-β type II receptor
TGF-β transforming growth factor-β
TR-FRET time-resolved fluorescence resonance energy transfer II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Aberrant (TGF-β signaling): Abnormal or dysregulated TGF-β signaling. In the context of the present disclosure, "aberrant TGF-β signaling" refers to excessive (pathological) activation of the TGF-β signaling pathway.

Administration: To provide or give a subject an agent, such as a therapeutic agent (e.g. a recombinant TGF-β), by any effective route. Exemplary routes of administration include, but are not limited to, injection or infusion (such as subcutaneous, intramuscular, intradermal, intraperitoneal, intrathecal, intravenous, intracerebroventricular, intrastriatal, intracranial and into the spinal cord), oral, intraductal, sublingual, rectal, transdermal, intranasal, vaginal and inhalation routes.

Contacting: Placement in direct physical association; includes both in solid and liquid form. When used in the context of an in vivo method, "contacting" also includes administering.

Fibrosis: The formation of excess fibrous connective tissue in an organ or tissue in a reparative or reactive process. Fibrosis can occur in many different tissues of the body (such as heart, lung and liver), typically as the result of inflammation or damage. Fibrotic disorders include, but are not limited to, pulmonary fibrosis, cystic fibrosis, idiopathic pulmonary fibrosis, interstitial lung disease, liver cirrhosis, kidney fibrosis (such as from damage caused by diabetes), atrial fibrosis, endomyocardial fibrosis, atherosclerosis, restenosis and scleroderma. Fibrosis can also occur as a result of surgical complications, chemotherapeutic drugs, radiation, injury or burns.

Fusion protein: A protein comprising at least a portion of two different (heterologous) proteins. In some embodiments herein, the fusion protein includes a TGF-β monomer fused to a protein tag, an Fc domain (such as a human Fc domain) or albumin.

Glycosylation: The process of covalent attachment of carbohydrate moieties to an asparagine (N-glycosylation), or serine or threonine residue (O-glycosylation). The level and type of glycosylation can vary in different host organisms used for recombinant expression. Novel glycosylation site can be sequence engineered by introducing glycosylation sequons in solvent exposed regions of the protein. For example, the N-glycosylation sequon NX[S/T] can be introduced at one or more places within the sequence of certain embodiments disclosed herein. Varying the type and extent of glycosylation has practical application in modulating solubility, function and half-life, as well as enabling site-specific chemical conjugation.

Heterologous: Originating from a separate genetic source or species.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Monomer: A single molecular unit (such as a protein) that is capable of binding to other molecular units to form dimers or polymers. In the context of the present disclosure, a "TGF-β monomer" is a single TGF-β polypeptide chain, the wild-type version of which can bind other TGF-β monomers to form dimers. In some embodiments herein, the recombinant TGF-β monomers have been engineered to prevent dimerization. In other embodiments herein, the recombinant TGF-β monomers which have been engineered to prevent their direct dimerization can be fused to heterologous proteins that are themselves capable of dimerization (e.g., an Fc domain of an IgG).

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

PEGylation: The process of both covalent and non-covalent attachment or amalgamation of polyethylene glycol (PEG) polymer chains to molecules and macrostructures, such as a drug, therapeutic protein or vesicle, which is then referred to as PEGylated (or pegylated). PEGylation is routinely achieved by incubation of a reactive derivative of PEG with the target molecule. The covalent attachment of PEG to a drug or therapeutic protein can mask the agent from the host's immune system (reduced immunogenicity and antigenicity), and increase the hydrodynamic size (size in solution) of the agent, which prolongs its circulatory time by reducing renal clearance. PEGylation can also provide water solubility to hydrophobic drugs and proteins.

Peptide or Polypeptide: A polymer in which the monomers are amino acid residues which are joined together through amide bonds. When the amino acids are alpha-amino acids, either the L-optical isomer or the D-optical isomer can be used, the L-isomers being preferred. The terms "peptide," "polypeptide" or "protein" as used herein are intended to encompass any amino acid sequence and include modified sequences, including modified globin proteins. The terms "peptide" and "polypeptide" are specifically intended to cover naturally occurring proteins, as well as those which are recombinantly or synthetically produced.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, serine or threonine, is substituted for (or by) a hydrophobic residue, for example, leucine, isoleucine, phenylalanine, valine or alanine; (b) a cysteine or proline is substituted for (or by) any other residue; (c) a residue having an electropositive side chain, for example, lysine, arginine, or histidine, is substituted for (or by) an electronegative residue, for example, glutamine or aspartic acid; or (d) a residue having a bulky side chain, for example, phenylalanine, is substituted for (or by) one not having a side chain, for example, glycine.

Pharmaceutically acceptable carriers: The pharmaceutically acceptable carriers of use are conventional. *Remington's Pharmaceutical Sciences*, by E. W. Martin, Mack Publishing Co., Easton, PA, 15th Edition, 1975, describes compositions and formulations suitable for pharmaceutical delivery of the compositions disclosed herein.

In general, the nature of the carrier will depend on the particular mode of administration being employed. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease.

Recombinant: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques. The term recombinant includes nucleic acids and proteins that have been altered by addition, substitution, or deletion of a portion of a natural nucleic acid molecule or protein.

Sequence identity/similarity: The identity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and C. elegans sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Subject: Living multi-cellular organisms, including vertebrate organisms, a category that includes both human and non-human mammals.

Tag: A molecule that can be attached to a protein or nucleic acid, such as for labeling, detection or purification purposes. In some embodiments, the tag is a protein tag. In some embodiments, the protein tag is an affinity tag (for example, Avitag, hexahistidine, chitin binding protein, maltose binding protein, or glutathione-S-transferase), an epitope tag (for example, V5, c-myc, HA or FLAG) or a fluorescent tag (e.g., GFP or another well-known fluorescent protein).

Therapeutically effective amount: A quantity of compound or composition, for instance, a recombinant TGF-β monomer, sufficient to achieve a desired effect in a subject being treated. For instance, this can be the amount necessary to inhibit or block TGF-β signaling in a cell.

Transforming growth factor-β (TGF-β): A secreted, multifunctional protein that regulates proliferation, cellular differentiation and a number of other cellular functions. Many cells synthesize TGF-β and nearly all cells express receptors for TGF-β. The term "TGF-β" refers to three different protein isoforms, TGF-β1, TGF-β2 and TGF-β3, encoded by the genes TGFB1, TGFB2, TGFB3, respectively.

TGF-β signaling pathway: A signaling pathway involved in a number of cellular processes, such as cell proliferation, differentiation and apoptosis. Members of the TGF-β pathway include, but are not limited to, TGF-β1, TGF-β2, TGF-β3 and TGF-β receptor type I and TGF-β receptor type II.

TGF-β receptor: The term "TGF-β receptor" includes TGF-β receptor type I (encoded by TGFBR1) and TGF-β receptor type II (encoded by TGFBR2). TGF-β receptors are serine/threonine protein kinases. The type I and type II TGF-β receptors form a heterodimeric complex when bound to TGF-β, transducing the TGF-β signal from the cell surface to the cytoplasm.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Disclosed herein are recombinant transforming growth factor (TGF)-β monomers that are modified to inhibit dimerization and type I receptor binding, but retain the capacity to bind the high affinity TGF-β type II receptor (TβRII). The recombinant TGF-β monomers disclosed herein can be used to inhibit TGF-β signaling, such as for the treatment of diseases or disorders characterized by aberrant TGF-β signaling, for example fibrotic disorders, ocular diseases, certain types of cancer, or a genetic disorder of connective tissue. In addition, nucleic acid molecules encoding a recombinant TGF-β monomer can be used to reprogram T cells to overproduce the recombinant protein. T cells engineered to overexpress the recombinant TGF-β monomer can be used in gene therapy applications, such as for the treatment of diseases or disorders characterized by aberrant TGF-β signaling.

Provided herein is a recombinant TGF-β monomer that includes a cysteine to serine substitution at amino acid residue 77 (with reference to SEQ ID NO: 2); a deletion of amino acid residues 52-71 (with reference to SEQ ID NO: 2); and at least one amino acid substitution (for example, a substitution proximal to the deleted residues) relative to a wild-type TFG-β monomer that increases net charge of the monomer. The cysteine to serine substitution prevents disulfide bond formation between TGF-β monomers. The deletion of amino acid residues 52-71 removes the α-helical 3 (α3) region (the primary dimerization motif), as well as a few flanking residues (FIG. 1D). When residues 52-71 are removed, the remaining residues form a loop that contains polar and charged residues (FIGS. 1D and 2B).

In some embodiments, the TGF-β monomer is a human, mouse, rat or other mammalian TGF-β monomer.

In some embodiments, the TGF-β monomer further includes at least one amino acid substitution relative to a wild-type TFG-β2 monomer that increases affinity of the TGF-β monomer for TβRII.

In some embodiments, the TGF-β monomer is a human TGF-β2 monomer. In some examples, the at least one amino acid substitution that increases net charge of the human TGF-β2 monomer includes a leucine to arginine substitution at residue 51; an alanine to lysine substitution at residue 74; or both a leucine to arginine substitution at residue 51 and an alanine to lysine substitution at residue 74 (with reference to SEQ ID NO: 2).

In some embodiments, the at least one amino acid substitution that increases affinity of the human TGF-β2 monomer for TβRII includes a substitution at an amino acid residue corresponding to residue 23, 24, 25, 26, 27, 28, 29, 30, 31, 32, 33, 34, 35, 36, 37, 89, 90, 91, 92, 93, 94, 95, 96, 97, 98 or 99 of SEQ ID NO: 2, or any combination of two or more residues thereof. In some examples, the at least one amino acid substitution that increases affinity of the monomer for TβRII comprises at least one substitution at residue 23, 24, 25, 26, 27, 28, 29, 30, 31, 32, 33, 34, 35, 36 or 37, and at least one substitution at residue 89, 90, 91, 92, 93, 94, 95, 96, 97, 98 or 99. In specific examples, the at least one amino acid substitution that increases affinity of the human TGF-β2 monomer for TβRII includes a lysine to arginine at residue 25, an arginine to lysine at residue 26, a leucine to valine at residue 89, an isoleucine to valine at residue 92, an asparagine to arginine at residue 94, a threonine to lysine at residue 95, an isoleucine to valine at residue 98, or any combination of two or more thereof, such as three or more, four or more, five or more, or six or more. In one non-limiting examples, the recombinant human TGF-β2 monomer includes a lysine to arginine at residue 25, an arginine to lysine at residue 26, a leucine to valine at residue 89, an isoleucine to valine at residue 92, an asparagine to arginine at residue 94, a threonine to lysine at residue 95, and an isoleucine to valine at residue 98.

In some examples, the amino acid sequence of the human TGF-β2 monomer is at least 95%, at least 96%, at least 97%, at least 98%, or at least 99% identical to SEQ ID NO: 8 or SEQ ID NO: 10. In some instances, the human TGF-β2 monomer is at least 95%, at least 96%, at least 97%, at least 98%, or at least 99% identical to SEQ ID NO: 8 or SEQ ID NO: 10 and contains only conservative amino acid substitutions. In particular non-limiting examples, the amino acid sequence of the human TGF-β2 monomer comprises or consists of SEQ ID NO: 8 or SEQ ID NO: 10.

In other embodiments, recombinant TGF-β monomer is a human TGF-β1 monomer. In some examples, the at least one amino acid substitution that increases net charge of the human TGF-β1 monomer includes an isoleucine to arginine substitution at residue 51; an alanine to lysine substitution at residue 74; an alanine to serine substitution at residue 75; or an isoleucine to arginine substitution at residue 51, an alanine to lysine substitution at residue 74 and an alanine to serine substitution at residue 75 (with reference to SEQ ID NO: 1).

In some examples, the amino acid sequence of the human TGF-β1 monomer is at least 95%, at least 96%, at least 97%, at least 98%, or at least 99% identical to SEQ ID NO: 7. In some instances, the human TGF-β1 monomer is at least 95%, at least 96%, at least 97%, at least 98%, or at least 99% identical to SEQ ID NO: 7 and contains only conservative amino acid substitutions. In particular non-limiting examples, the amino acid sequence of the human TGF-β1 monomer comprises or consists of SEQ ID NO: 7.

In other embodiments, the recombinant TGF-β monomer is a human TGF-β3 monomer. In some examples, the at least one amino acid substitution that increases net charge of the human TGF-β3 monomer includes a leucine to glutamate substitution at residue 51; an alanine to glutamate substitution at residue 72; an alanine to aspartate substitution at residue 74; or a leucine to glutamate substitution at residue 51, an alanine to glutamate substitution at residue 72 and an alanine to aspartate substitution at residue 74 (with reference to SEQ ID NO: 3).

In some examples, the amino acid sequence of the human TGF-β3 monomer is at least 95%, at least 96%, at least 97%, at least 98%, or at least 99% identical to SEQ ID NO: 9. In some instances, the human TGF-β3 monomer is at least 95%, at least 96%, at least 97%, at least 98%, or at least 99% identical to SEQ ID NO: 9 and contains only conservative amino acid substitutions. In particular non-limiting examples, the amino acid sequence of the human TGF-β3 monomer comprises or consists of SEQ ID NO: 9.

In some embodiments herein, the recombinant TGF-β monomer is PEGylated, glycosylated, hyper-glycosylated, or includes another modification that prolongs circulatory time.

Also provided herein are fusion proteins that include a TGF-β monomer and a heterologous protein. In some embodiments, the heterologous protein is a protein tag. In some examples, the protein tag is an affinity tag (for example, Avitag, hexahistidine, chitin binding protein, maltose binding protein, or glutathione-S-transferase), an epitope tag (for example, V5, c-myc, HA or FLAG) or a fluorescent tag (e.g., GFP or another well-known fluorescent protein). In other embodiments, the heterologous protein comprises an Fc domain, such as a mouse or human Fc domain. In specific embodiments, the heterologous protein promotes intermolecular association into homodimeric (for example, Fc domain from human IgG1, IgG2, IgG3), heterodimeric (for example, an engineered Fc domain, E/K coiled-coil), or multimeric (for example, pentabodies, nanoparticles) states of the fusion protein. In other embodiments, the heterologous protein is albumin, an albumin-binding protein or agent, or another protein that increases circulatory time of the TGF-β monomer in vivo.

Also provided are recombinant TGF-β monomers or fusion proteins comprising a radiotherapy agent, a cytotoxic agent for chemotherapy, or a drug. Further provided are recombinant TGF-β monomers or fusion proteins comprising an imaging agent, a fluorescent dye, or a fluorescent protein tag.

Further provided herein is a composition, such as a pharmaceutical composition, that includes a recombinant TGF-β monomer or fusion protein disclosed herein, and a pharmaceutically acceptable carrier, diluent or excipient.

Also provided herein is a method of inhibiting TGF-β signaling in a cell. In some embodiments, the method includes contacting the cell with a recombinant TGF-β monomer, fusion protein or composition disclosed herein.

In some embodiments, the method is an in vitro method.

In other embodiments, the method is an in vivo method. In some examples, the in vivo method includes administering the recombinant TGF-β monomer, fusion protein or composition to a subject having a disease or disorder associated with aberrant TGF-β signaling. In some examples, the recombinant TGF-β monomer, fusion protein or composition is administered by injection, such as by subcutaneous, intramuscular, intradermal, intraperitoneal, intravenous or intratumoral injection.

Also provided is a method of treating a disease or disorder associated with aberrant TGF-β signaling. In some embodiments, the method includes administering a recombinant TGF-β monomer, fusion protein or composition disclosed herein to a subject.

In some embodiments, the disease or disorder associated with aberrant TGF-β signaling is a fibrotic disorder, such as but not limited to, pulmonary fibrosis, cystic fibrosis, idiopathic pulmonary fibrosis, interstitial lung disease, liver cirrhosis, kidney fibrosis (such as from damage caused by diabetes), atrial fibrosis, endomyocardial fibrosis, atherosclerosis, restenosis, scleroderma, or fibrosis caused by a surgical complication, chemotherapeutic drugs, radiation, injury or burns.

In other embodiments, the disease or disorder associated with aberrant TGF-β signaling is breast cancer, brain cancer, pancreatic cancer, prostate cancer, skin cancer, bladder cancer, liver cancer, ovarian cancer, renal cancer, endometrial cancer, colorectal cancer, gastric cancer, skin cancer (such as malignant melanoma), or thyroid cancer.

In other embodiments, the disease or disorder associated with aberrant TGF-β signaling is an ocular disease.

In other embodiments, the disease or disorder associated with aberrant TGF-β signaling is a genetic disorder of connective tissue.

Further provided are isolated nucleic acid molecules encoding a recombinant TGF-β monomer disclosed herein. In some embodiments, the nucleic acid molecule is operably linked to a promoter, such as a T cell specific promoter.

Also provided are vectors that include a TGF-β monomer-encoding nucleic acid molecule. In some embodiments, the vector is a viral vector, such as a lentiviral vector.

Isolated cells, such as, but not limited to, isolated T cells comprising a nucleic acid molecule or vector encoding a recombinant TGF-β monomer disclosed herein are further provided. The cells can be autologous to the subject, or they can be heterologous (allogeneic). Compositions that include the isolated cells and a pharmaceutically acceptable carrier are also provided.

Further provided are methods of treating a disease or disorder associated with aberrant TGF-β signaling in a subject. In some embodiments, the method includes administering to the subject a nucleic acid molecule, vector or isolated cell disclosed herein. In some examples, the disease or disorder associated with aberrant TGF-β signaling is a fibrotic disorder. In other examples, the disease or disorder associated with aberrant TGF-β signaling is breast cancer, brain cancer, pancreatic cancer, prostate cancer or skin cancer. In other examples, the disease or disorder associated with aberrant TGF-β signaling is an ocular disease. In yet other examples, the disease or disorder associated with aberrant TGF-β signaling is a genetic disorder of connective tissue.

IV. Administration of Engineered TGF-β Monomers

Compositions, such as pharmaceutical compositions, that include a recombinant human TGF-β monomer or fusion protein, are provided herein. Also provided are compositions that include an isolated cell, such as a T cell, comprising a vector encoding a recombinant human TGF-β monomer. In some embodiments, the composition includes a pharmaceutically acceptable carrier.

The pharmaceutically acceptable carriers and excipients useful in this disclosure are conventional. See, e.g., Remington: The Science and Practice of Pharmacy, The University of the Sciences in Philadelphia, Editor, Lippincott, Williams, & Wilkins, Philadelphia, PA, 21$^{st}$ Edition (2005). For instance, parenteral formulations usually comprise injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, other proteins, such as human serum albumin or plasma preparations.

With regard to administration of cells, a variety of aqueous carriers can be used, for example, buffered saline and the like, for introducing the cells. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration in these formulations can vary widely, and will be selected primarily based on fluid volumes, viscosities, body weight and the like in accordance with the particular mode of administration selected and the subject's needs.

The dosage form of the composition will be determined by the mode of administration chosen. For instance, in addition to injectable fluids, topical, inhalation, oral and suppository formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

The compositions, such as pharmaceutical compositions, that include a recombinant human TGF-β monomer, can be formulated in unit dosage form, suitable for individual administration of precise dosages. The amount of TGF-β monomer administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The TGF-β monomers, or compositions thereof, can be administered to humans or other animals on whose tissues they are effective in various manners such as topically, orally, intravenously, intramuscularly, intraperitoneally, intranasally, intradermally, intrathecally, subcutaneously, via inhalation or via suppository. The particular mode of administration and the dosage regimen will be selected by the attending clinician, taking into account the particulars of the case (e.g. the subject, the disease, the disease state involved, and whether the treatment is prophylactic). Treatment can involve daily or multi-daily doses of compound(s) over a period of a few days to months, or even years.

The following examples are provided to illustrate certain particular features and/or embodiments. These examples should not be construed to limit the disclosure to the particular features or embodiments described.

EXAMPLES

Example 1: An Engineered TGF-β Monomer that Functions as a Dominant Negative to Block TGF-β Signaling This example describes an engineered TGF-β monomer that is capable of blocking TGF-β signaling. The engineered TGF-β monomer, referred to herein as mmTGF-β2-7M, has three changes relative to the monomer of wild type dimeric TGF-β2:

(1) The cysteine that normally forms the inter-chain disulfide (Cys77) was substituted with serine (FIG. 1D);
(2) The α3 helix was eliminated and replaced with a short loop bearing polar and charged residues (FIG. 1D); and
(3) Seven residues were substituted relative to TGF-β2 that enabled high affinity TβRII binding (FIG. 1E).

The features of mmTGF-β2-7M and other engineered TGF-β variants disclosed herein are described below and listed in Table 1. The sequences of all engineered TGF-β variants are shown in FIG. 8 and set forth as SEQ ID NOs: 1-11.

Background

Previous studies showed that wild type TGF-β1 and TGF-β3 monomers (that is TGF-β1 and TGF-β3 monomers with the cysteine residue that normally forms the interchain disulfide, Cys77, substituted to serine) were about 10-15 fold less potent compared to the naturally occurring disulfide-linked homodimers, yet they nonetheless retained significant signaling activity, with midpoint stimulatory potencies ($EC_{50}$s) of about 150 pM (Amatayakul-Chantler et al., *J Biol Chem* 269:27687-27691, 1994; Zúñiga et al., *J Mol Biol* 355:47-62, 2006).

Based on structural studies, it was not clear why TGF-β1 Cys77→Ser and TGF-β3 Cys77→Ser variants would retain such significant signaling activity since one of the two essential receptors that binds to the growth factor, the TGF-β type I receptor (TβRI) was shown to bind by straddling the TGF-β homodimer interface (FIG. 1A) (Groppe et al., *Mol Cell* 29:157-168, 2008).

It was hypothesized that the TGF-β monomers were signaling by non-covalently dimerizing and binding the receptors, which in turn stabilized the noncovalent dimers (by virtue of the fact that at least one of them, TβRI, binds across the dimer interface). To generate a TGF-β monomer that would function as an inhibitor, rather than a stimulator of TGF-beta signaling, an engineered monomer was produced in which the primary dimerization motif, the interfacial α-helix, α3, was replaced with a flexible loop (FIGS. 1A and 1D). It was reasoned that this would interfere with the ability of TGF-β to dimerize and recruit TβRI by (a) limiting the potential of the monomers to non-covalently dimerize due to hydrophobic contacts (FIG. 1B) and (b) by eliminating a significant portion of the contact surface for the TGF-β type I receptor, TβRI, that binds by straddling the TGF-beta dimer interface (FIG. 1C).

Methods

Protein Expression and Purification

TGF-β1 was expressed as a secreted protein bound to its prodomain in stably transfected Chinese hamster ovary (CHO) cells. The cell line used to produce TGF-β1, and the accompanying procedure to isolate the mature disulfide-linked TGF-β1 homodimer from the conditioned medium has been previously described (Zou and Sun, *Protein Expr Purif* 37, 265-272, 2004). Human homodimeric TGF-β2 (TGF-β2), human homodimeric TGF-β3 (TGF-β3), and variants, including avi-tagged (Cull and Schatz, *Methods Enzymol* 326, 430-440, 2000) homodimeric TGF-β3 (TGF-β3-avi), monomeric TGF-β2 (mTGF-β2), monomeric TGF-β2 (mTGF-β3), mini monomeric TGF-β1 (mmTGF-β1), mini monomeric TGF-β2 (mmTGF-β2), mini monomeric TGF-β3 (mmTGF-β3), mini monomeric TGF-β2 with seven substitutions to enable high affinity TβRII binding (mmTGF-β2-7M), and avi-tagged (Cull and Schatz, *Methods Enzymol* 326, 430-440, 2000) mini monomeric TGF-β2 with seven substitutions to enable high affinity TβRII binding (mmTGF-β2-7M) were expressed in *E. coli*, refolded from inclusion bodies into native folded disulfide-linked homodimers (TGF-β2, TGF-β3, TGF-β3-avi) or monomers (mTGF-β1, mTGF-β2, mTGF-β3, mmTGF-β1, mmTGF-β2, mmTGF-β3, mmTGF-β2-7M, mmTGF-β2-7M-avi), and purified to homogeneity using high resolution cation exchange chromatography (Source Q, GE Healthcare, Piscataway, NJ) as previously described (Huang and Hinck, *Methods Mol Biol* 1344, 63-92, 2016). The nomenclature and major features of the dimeric and monomeric TGF-β used in this study are summarized in Table 1, and the complete sequences are shown in FIG. 8.

TABLE 1

| TGF-β variants | | | | | |
|---|---|---|---|---|---|
| Variant Name (SEQ ID NO) | Variant Description | Number Residues per Monomer | Single amino acid substitution(s) | Deletion | Tag |
| TGF-β1 (1) | Human TGF-β1 wild type homodimer | 112 | None | None | None |
| TGF-β2 (2) | Human TGF-β2 wild type homodimer | 112 | None | None | None |
| TGF-β3 (3) | Human TGF-β3 wild type homodimer | 112 | None | None | None |

TABLE 1-continued TGF-β variants

| Variant Name (SEQ ID NO) | Variant Description | Number Residues per Monomer | Single amino acid substitution(s) | Deletion | Tag |
|---|---|---|---|---|---|
| avi-TGF-β3 (4) | Human TGF-β3 wild type homodimer with N-terminal Avitag | 127 | None | None | N-terminal Avitag |
| mTGF-β2 (5) | Human TGF-β2 covalent monomer | 112 | C77S | None | None |
| mTGF-β3 (6) | Human TGF-β3 covalent monomer | 112 | C77S | None | None |
| mmTGF-β1 (7) | Human TGF-β1 covalent monomer with α3 replaced with a loop | 92 | I51R, A74K, A75S, C77S | Residues 52-71 | None |
| mmTGF-β2 (8) | Human TGF-β2 covalent monomer with α3 replaced with a loop | 92 | L51R, A74K, C77S | Residues 52-71 | None |
| mmTGF-β3 (9) | Human TGF-r33 covalent monomer with α3 replaced with a loop | 92 | L51E, A72E, A74D, C77S | Residues 52-71 | None |
| mmTGF-β2-7M (10) | Human TGF-β2 covalent monomer with α3 replaced with a loop | 92 | R26K, L51R, A74K, C77S, L89V, I92V, N94R T95K, I98V, K25R | Residues 52-71 | None |
| avi-mmTGF-β2-7M (11) | Human TGF-r32 covalent monomer with α3 replaced with a loop | 107 | R26K, L51R, A74K, C77S, L89V, I92V, N94R T95K, I98V, K25R | Residues 52-71 | N-terminal Avitag |

The human TβRI ectodomain (TβRI), spanning residues 1-101 of the mature receptor, or a variant spanning residues 1-88 of the mature receptor with a 15 amino acid avitag (Cull and Schatz, *Methods Enzymol* 326, 430-440, 2000) appended to the C-terminus (TβRI-ΔC-Avi) was expressed in *E. coli*, refolded from inclusion bodies, and purified to homogeneity as previously described (Zúñiga et al., *J Mol Biol* 354, 1052-1068, 2005). The human TβRII ectodomain (TβRII), spanning residues 15-136 of the mature receptor, or the same but with a C-terminal hexahistidine tag (TβRII-His) was expressed in *E. coli*, refolded from inclusion bodies, and purified to homogeneity as previously described (Hinck et al., *J Biomol NMR* 18, 369-370, 2000).

Solubility Assays

TGF-β dimers and monomers were concentrated in 100 mM acetic acid to concentrations of 300 μM or higher and diluted to the desired concentration in either 100 mM acetic acid or phosphate buffered saline (PBS, 10 mM $Na_2HPO_4$, 1.8 mM $KH_2PO_4$, 137 mM NaCl, 2.7 mM KCl, pH 7.4). The pH of the samples diluted into PBS were adjusted with small aliquots of NaOH to ensure a final pH of 7.4. The light scattering at 340 nm of the samples were measured using a HP 8452 diode array spectrophotometer (HP, Palo Alto, CA). The samples were transferred to a microfuge tube, centrifuged at 20000× g for 5 minutes and the absorbance at 280 nm of the supernatant was measured using a NANODROP™ spectrophotometer (ThermoFisher, Waltham, MA). Results of solubility assays are shown in FIGS. 4A-4D.

Nuclear Magnetic Resonance (NMR) Spectroscopy mmTGF-β2 and mmTGF-β2-7M samples isotopically labeled with $^{15}N$ or $^{15}N$ and $^{13}C$ for NMR were prepared by growing bacterial cells in M9 media containing 0.1% (w/v) $^{15}NH_4Cl$ or 0.1% (w/v) $^{15}NH_4Cl$ and 0.03% (w/v) $^{13}C$ labeled glucose. All NMR samples were prepared in 10 mM sodium phosphate, 10 mM 3-[(3-cholamidopropyl)dimethylammonio]-1-propanesulfonate (CHAPS), 5% $^2H_2O$, 0.02% w/v sodium azide at a protein concentration of 0.2 mM-0.4 mM, pH 4.7. All NMR data was acquired at a sample temperature of 37° C. at either 700 or 800 MHz. Backbone resonance assignments of mmTGF-β2 and mmTGF-β2-7M were obtained by collecting and analyzing sensitivity-enhanced HNCACB (Wittekind and Mueller, *J Magn Reson Ser B* 101:201-205, 1993), CBCA(CO)NH (Grzesiek et al., *J Magn Reson Ser B* 101:114-119, 1993), C(CO)NH (Grzesiek and Bax, *J Biomol NMR* 3:185-204, 1993), HNCO (Kay et al., *J Magn Reson* 89:496-514, 1990), data sets with 25% non-uniform sampling (NUS) of the points in the $^{13}C$, $^{15}N$ acquisition grid. Backbone amide $^{15}N$ $T_2$ relaxation parameters were measured in an interleaved manner at 300° K at a $^{15}N$ frequency of 70.95 MHz using $^1H$-detected pulse schemes previously described (Kay et al., *Biochemistry* 28:8972-8979, 1989). The $T_2$ data sets were each collected using 8-10 delay times, varying between 16-192 ms. The $T_2$ relaxation times were obtained by fitting relative peak intensities as a function of the $T_2$ delay time to a two parameter decaying exponential. Data was processed using NMRPipe (Delaglio et al., *J Biomol NMR* 6: 277-293, 1995), with the SMILE algorithm used for prediction of the missing points in the $^{13}$C and $^{15}$N dimensions of the NUS data sets (Ying et al., *J. Biomol. NMR* 2016). Data analysis was performed using NMRFAM-SPARKY (Lee et al., *Bioinformatics* 31:1325-1327, 2015).

SPR Binding Measurements

SPR measurements with TGF-β2 and mmTGF-β2 shown in FIGS. 3A-3B were performed using a BIACORE™ 3000 SPR (G.E. Healthcare, Piscataway, NJ) instrument with direct immobilization of TGF-β2 or mmTGF-β2 on the surface of a CM5 sensor chip (G.E. Healthcare, Piscataway, NJ) using an amine (carbodiimide-based) coupling kit (G.E. Healthcare, Piscataway, NJ). SPR experiments shown in FIGS. 3C, 3E and 3G and FIGS. 3D, 3F and 3H with TGF-β3 and mmTGF-β2-7m, respectively, were performed using a BIACORE™ X100 SPR instrument (G.E. Healthcare, Piscataway, NJ) with biotinylated ligands captured at a moderate density (50-200 RU) onto a streptavidin-coated CM5 sensor chip (GE Healthcare, Piscataway, NJ). Biotinylated TGF-β3 or mmTGF-β2-7M was generated by expressing TGF-β3 or mmTGF-β2-7M with an N-terminal 15 amino acid avitag (Cull and Schatz, *Methods Enzymol* 326, 430-440, 2000). TGF-β3-avi or mmTGF-β2-7M-avi was bound to TβRII in 10 mM bicine at pH 8.0 and biotinylated by incubating with a catalytic amount of bacterially expressed BirA recombinase, biotin, and ATP at 37° C. for 2 hours as described (Huang and Hinck, *Methods Mol Biol* 1344, 63-92, 2016). Biotinylated avi-tagged TGF-β3 or avi-tagged TGF-β2-7m were bound to a C4 reverse phase column equilibrated with 94.9% water/5% acetonitrile/0.1% triflouroacetic acid and eluted with a linear acetonitrile gradient.

SPR measurements shown in FIGS. 3A-3E were performed in HBS-EP buffer (10 mM HEPES, pH 7.4, 150 mM NaCl, 3 mM EDTA, 0.005% surfactant P20; GE Healthcare, Piscataway, NJ) with the receptor indicated injected over a series of two-fold dilutions over the concentration range shown. Injections were carried out in duplicate and included 10 buffer blank injections at the start of the experiment. Binding was allowed to associate for 2-3 minutes at a flow rate of 100 mL min$^{-1}$, followed by dissociation for 1 minute or longer. Each cycle of injection was followed by 10 ml of regeneration with 4 M guanidine•HCl, 2 M NaCl. Data was processed by subtracting both the response from a blank flow cell and buffer blanks using the program Scrubber2 (Biologic software, Campbell, Australia). Kinetic fitting of the data was performed with Scrubber2 assuming a simple 1:1 binding model. SPR measurements shown in FIGS. 3G and 3H were performed similarly, except 2 μM TβRII was included in both the running buffer and the injected samples. The results of SPR measurements are shown in Table 2 and FIGS. 3A-3H.

Crystallization, Structure Determination and Refinement

Crystals of mmTGF-β2 were formed in sitting drops at 25° C. by combining 0.2 μL of a 7.9 mg mL$^{-1}$ protein stock solution in 10 mM MES pH 5.5 with 0.2 μL of the precipitant from the well, 20% PEG 3350, 0.2 M sodium thiocyanate. Harvested crystals were mounted in undersized nylon loops with excess mother liquor wicked off, followed by flash-cooling in liquid nitrogen prior to data collection. Data were acquired at the Advanced Photon Source NE-CAT beamline 24-ID-C and integrated and scaled using XDS (Kabsch, *Acta Crystallogr D Biol Crystallogr* 66, 125-132, 2010). The structure was determined by the molecular replacement method implemented in PHASER (McCoy et al., *J Appl Crystallogr* 40, 658-674, 2007) using a truncated version of PDB entry 2TGI (Daopin et al., *Science* 257, 369-373, 1992) as the search model. Coordinates were refined using PHENIX (Adams et al., *Acta Crystallogr D Biol Crystallogr* 66, 213-221, 2010), including simulated annealing with torsion angle dynamics, and alternated with manual rebuilding using COOT (Emsley et al., *Acta Crystallogr D Biol Crystallogr* 66, 486-501, 2010). Data collection and refinement statistics are shown in Table 3.

Crystals of the mmTGF-β2-7M:TβRII complex were formed in hanging drops at 25° C. by combining 1.0 μL of a 7.4 mg mL$^{-1}$ stock solution of the complex in 10 mM Tris, pH 7.4 with 1.0 μL of 0.1 M HEPES, pH 7.5, 60% v/v (+/−)-2-Methyl-2,4-pentanediol. Harvested crystals were mounted in nylon loops, followed by flash-cooling in liquid nitrogen prior to data collection. Data were acquired at the Advanced Photon Source 24-ID-C and integrated and scaled using HKL2000 (Otwinowski and Minor, *Method Enzymol* 276, 307-326, 1997). The structure was determined by the molecular replacement method implemented in PHASER (McCoy et al., *J Appl Crystallogr* 40, 658-674, 2007) using TβRII (PDB 1M9Z; Boesen et al., *Structure* 10, 913-919, 2002) and mmTGF-β2 as search models. Coordinates were refined using PHENIX (Adams et al., *Acta Crystallogr D Biol Crystallogr* 66, 213-221, 2010), alternated with manual rebuilding using COOT (Emsley et al., *Acta Crystallogr D Biol Crystallogr* 66, 486-501, 2010). Data collection and refinement statistics are shown in Table 3.

Crystals of mmTGF-β2-7M were formed in hanging drops at 25° C. by combining 1.0 μL of a 10 mg mL$^{-1}$ protein stock solution in 20 mM acetic acid with 0.8 μL of the precipitant from the well, 100 mM sodium acetate dibasic trihydrate, pH 4.6, 25% 2-propanol, and 400 mM calcium chloride dehydrate, and 0.2 μL 5% n-ocyl-β-D-glucoside. Harvested crystals were mounted in nylon loops and cryo-protected in well buffer containing 20% glycerol and flash-cooled in a nitrogen stream. Data was collected at 100 K using a Rigaku FR-E Superbright generator equipped with a Saturn 944 CCD detector and processed using MOSFLM

TABLE 2

SPR binding parameters for TβRII and TβRI binding to dTGF-β3 and mmTGF-β27m

| Immobilized Ligand | Injected Receptor | Buffer | $k_a$ (M$^{-1}$ s$^{-1}$) | $k_d$ (s$^{-1}$) | $K_D$ (μM) | $R_{max}$ (RU) |
|---|---|---|---|---|---|---|
| avi-TGF-β3 | TβRII | HBS-EP | 1.16 × 10$^5$ | 0.0546 | 0.47 | 256 |
| avi-mmTGF-β2-7M | TβRII | HBS-EP | 2.64 × 10$^5$ | 0.1132 | 0.43 | 128 |
| avi-TGF-β3 | TβRI | HBS-EP + 2 μM TβRII | 4.64 × 10$^4$ | 0.0205 | 0.443 | 44 |
| avi-mmTGF-β2-7M | TβRI | HBS-EP + 2 μM TβRII | n.d.* | n.d.* | n.d.* | n.d.* |

*n.d.—no detectable response (Battye et al., *Acta Crystallogr D* 67, 271-281, 2011) in CCP4 (Winn et al., *Acta Crystallogr D* 67, 235-242, 2011). The structure of mmTGF-β2-7M was solved via molecular replacement using the structure of mmTGF-β2-7M from its co-crystal structure with TβRII. Iterative model building and refinement were performed using COOT (Emsley et al., *Acta Crystallogr D Biol Crystallogr* 66, 486-501, 2010) and PHENIX, respectively. Data collection and refinement statistics are shown in Table 3.

Figure 6A:
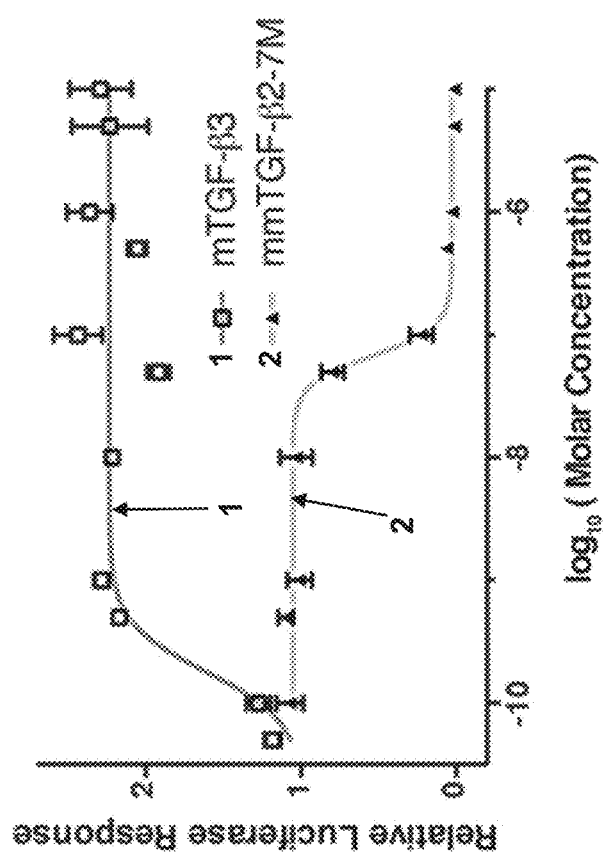
Figure 6B:
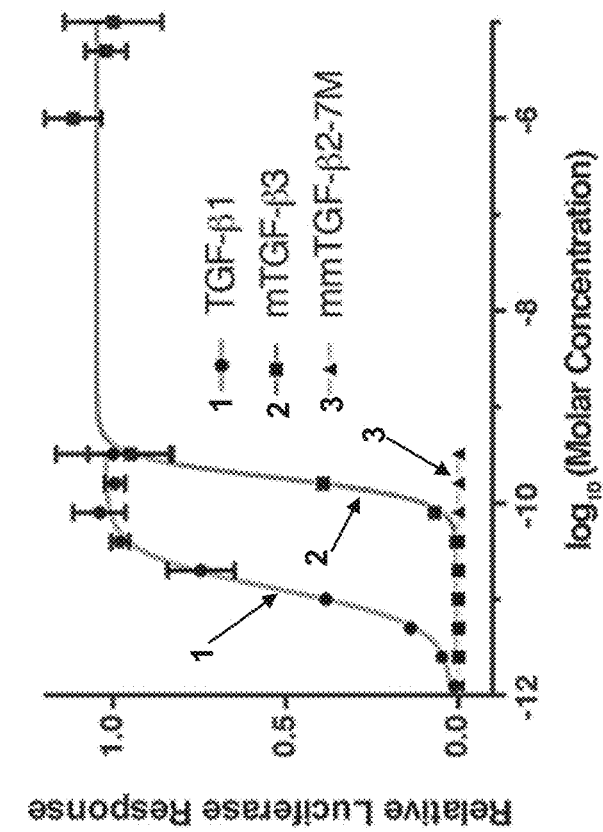

Results of structural studies are shown in FIGS. 2A-2D, 5A-5E, 9A-9B and 10A-10B.

presence of a constant sub-saturating concentration of TGF-β (TGF-β1, 8 pM; TGF-β2, 20 pM; TGF-β3, 10 pM). Proteins were diluted in DMEM containing 0.1% w/v BSA. After 16 hours, cells were lysed with Tropix lysis buffer (ThermoFisher, Waltham, MA) and luciferase activity was read with a Promega GloMax luminometer (Promega, Madison, WI). Luciferase activity was normalized to total protein levels determined by bicinchoninic acid (BCA) protein assay. Graphpad Prism 6 was used to fit the data to standard models for ligand activity ($EC_{50}$) and ligand inhibitory activity ($IC_{50}$) (Graphpad, La Jolla, CA). Results are shown in FIGS. 6A-6B.

TABLE 3

| X-ray Data collection and refinement statistics | | | |
|---|---|---|---|
| Data collection | | | |
| Molecule | mmTGF-β2 (PDB 5TX2) | mmTGF-β27m (PDB 5TX6) | mmTGF-β27m:TβRII (PDB 5TX4) |
| X-ray Source | Adv. Photon Source 24-ID-C | Rigaku 007 generator and Saturn 944 CCD detector | Adv. Photon Source SER-CAT 22-ID-D |
| Space group | C2 | P3$_1$21 | P2$_1$2$_1$2$_1$ |
| Cell dimensions | | | |
| a, b, c (Å) | 99.5, 33.4, 54.1 | 81.74, 81.74, 80.93 | 39.0, 70.8, 77.1 |
| α, β, γ (°) | 90, 109.6, 90 | 90, 90, 120 | 90, 90, 90 |
| Wavelength (Å) | 0.9795 | 1.542 | 0.97949 |
| Resolution (Å) | 51.01-1.82 (1.92-1.82)* | 36.48-2.75 (2.89-2.75)* | 35.39-1.88 |
| $R_{sym}$ | 0.050 (0.443) | 0.132 (0.463) | 0.143 (0.97)* |
| $R_{pim}$ | 0.038 (0.307) | 0.055 (0.232) | 0.058 (0.522) |
| I/σI | 12.7 (2.2) | 16.4 (4.0) | 15.17 (2.02) |
| Completeness (%) | 98.4 (98.4) | 99.9 (99.8) | 99.6 (99.4) |
| Redundancy | 3.6 (3.5) | 12.3 (8.9) | 6.8 (6.6) |
| Wilson value (Å$^2$) | 28.9 | 30.23 | 30.08 |
| Refinement | | | |
| Resolution (Å) | 51.01-1.82 | 36.48-2.75 | 35.39-1.88 |
| No. reflections | 15,027 | 8493 | 17,715 |
| $R_{work}/R_{free}$ | 0.209/0.252 | 0.2104/0.2694 | 0.1955/0.2216 |
| No. atoms | | | |
| Protein | 1,462 | 2,120 | 1,570 |
| Water | 107 | 63 | 82 |
| B-factors (Å$^2$) | | | |
| Protein | 33.3 | 42.6 | 43.6 |
| Water | 36.4 | 22.2 | 41.22 |
| R.m.s deviations | | | |
| Bond lengths (Å) | 0.012 | 0.006 | 0.011 |
| Bond angles (°) | 1.030 | 1.116 | 1.143 |
| Ramachandran statistics-favored, allowed, outliers (%) | 94.4, 5.0, 0.6 | 92.2, 7.8, 0.0 | 96.39, 3.09, 0.52 |

*Highest resolution shell is shown in parentheses

Luciferase Assays

Figure 7A:
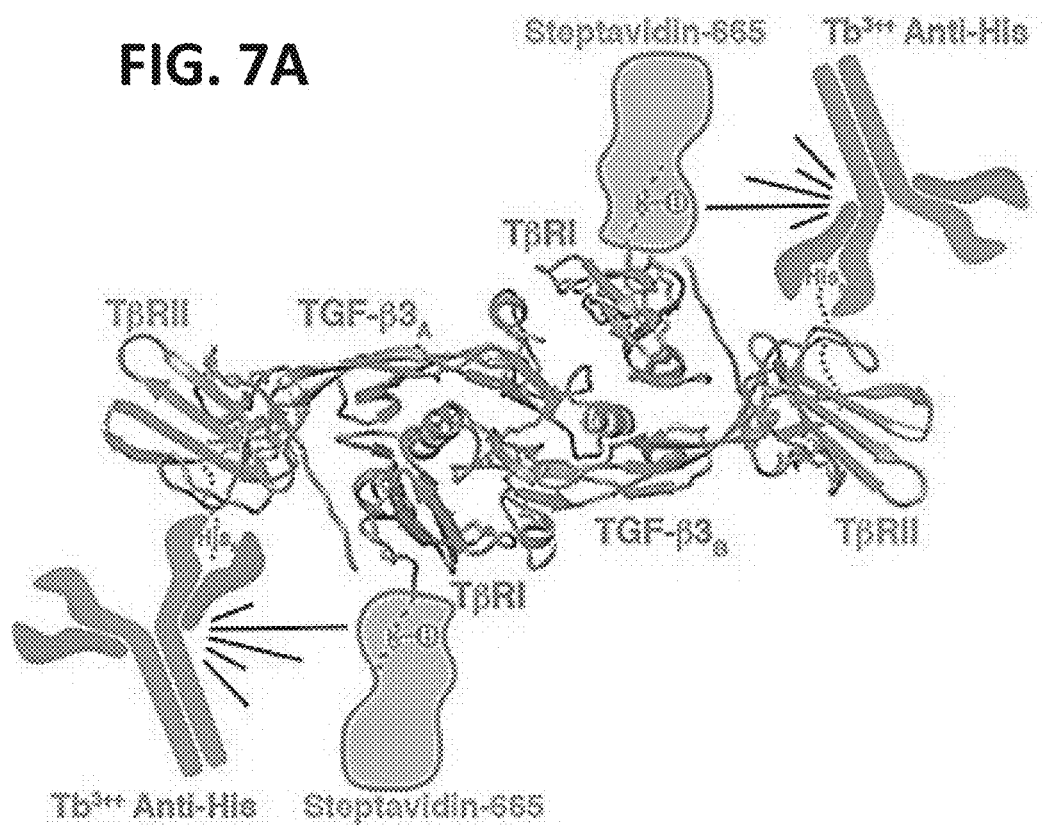
Figure 7B:
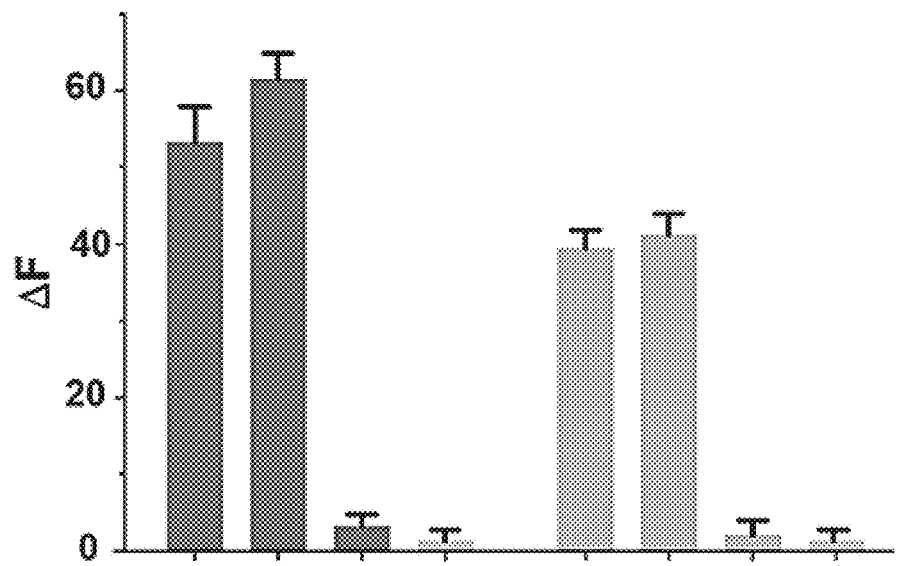
Figure 9A:
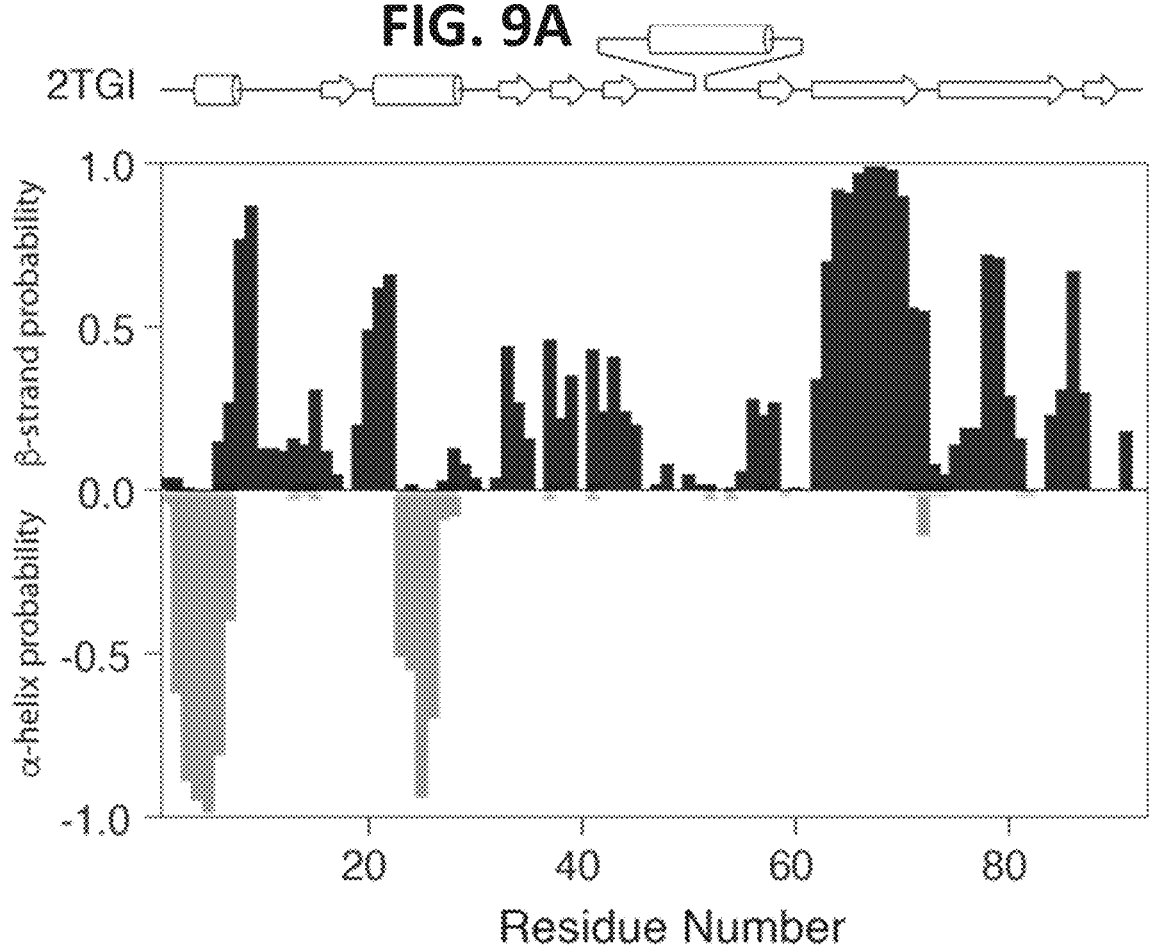
Figure 9B:
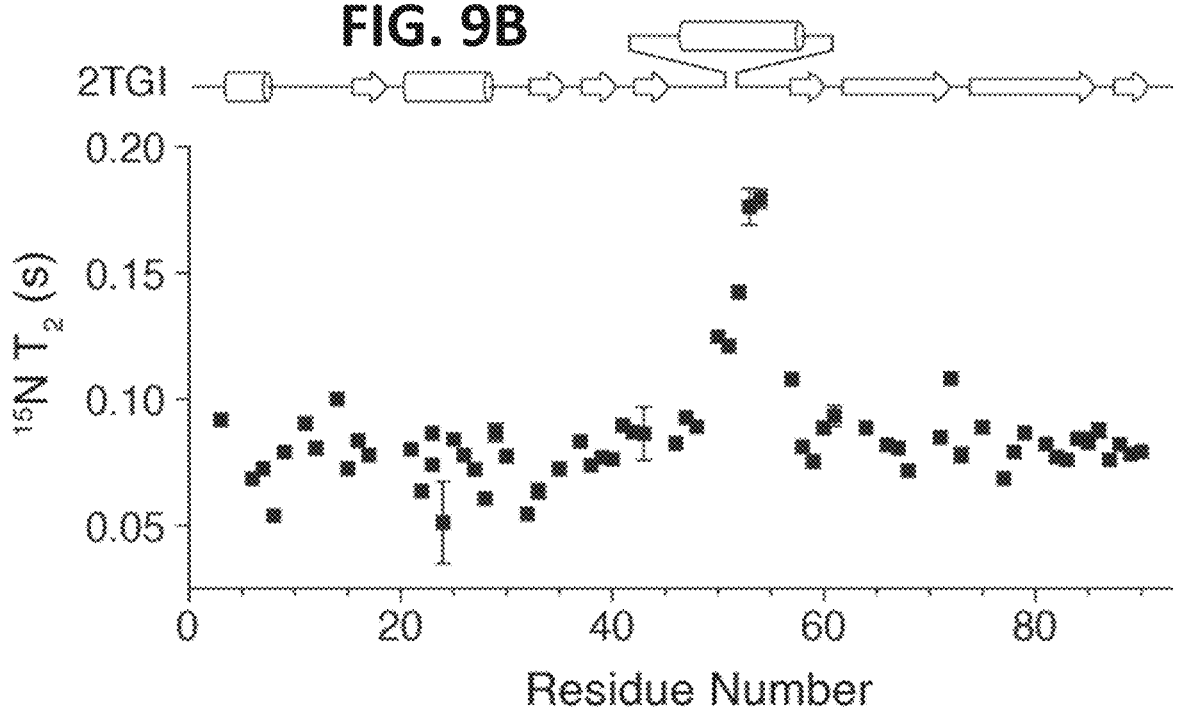
Figure 10A:
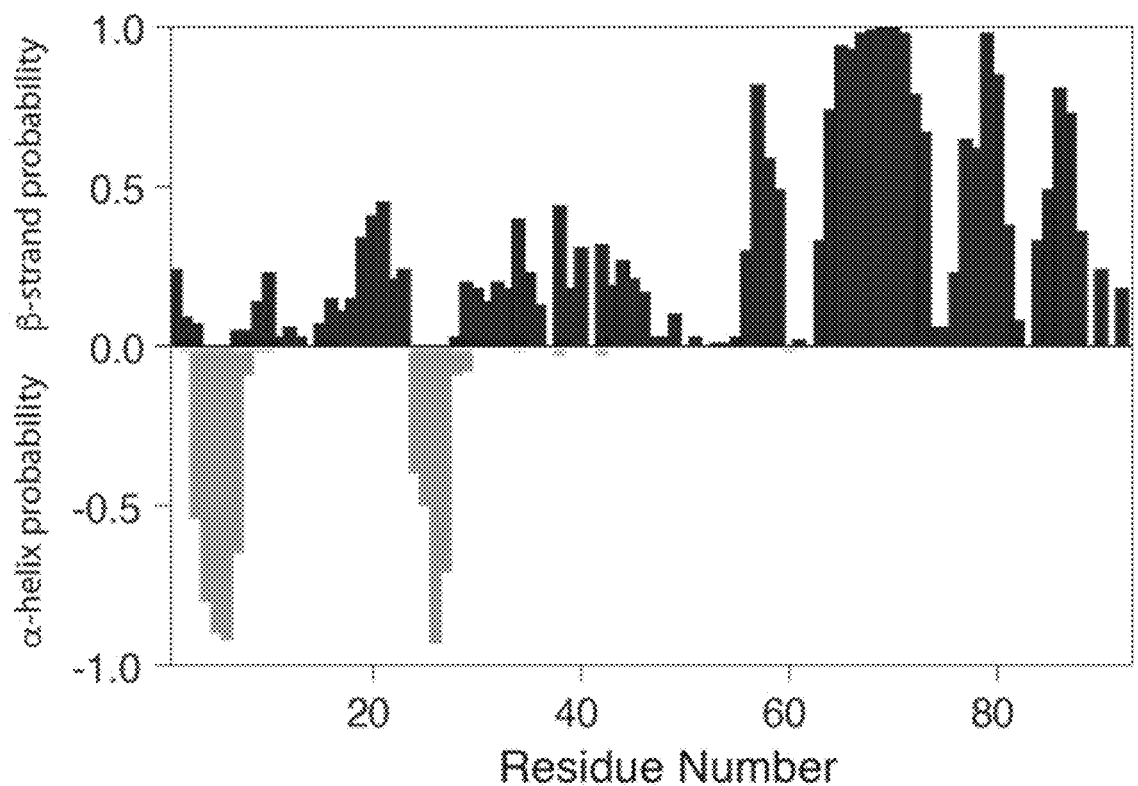
(FIG. 10B) $^{15}$N T$_2$ relaxation times plotted as a function of residue number. Secondary structures shown above each graph correspond to those from the crystal structure of TGF-β2 (PDB 2TGI).
Figure 10B:
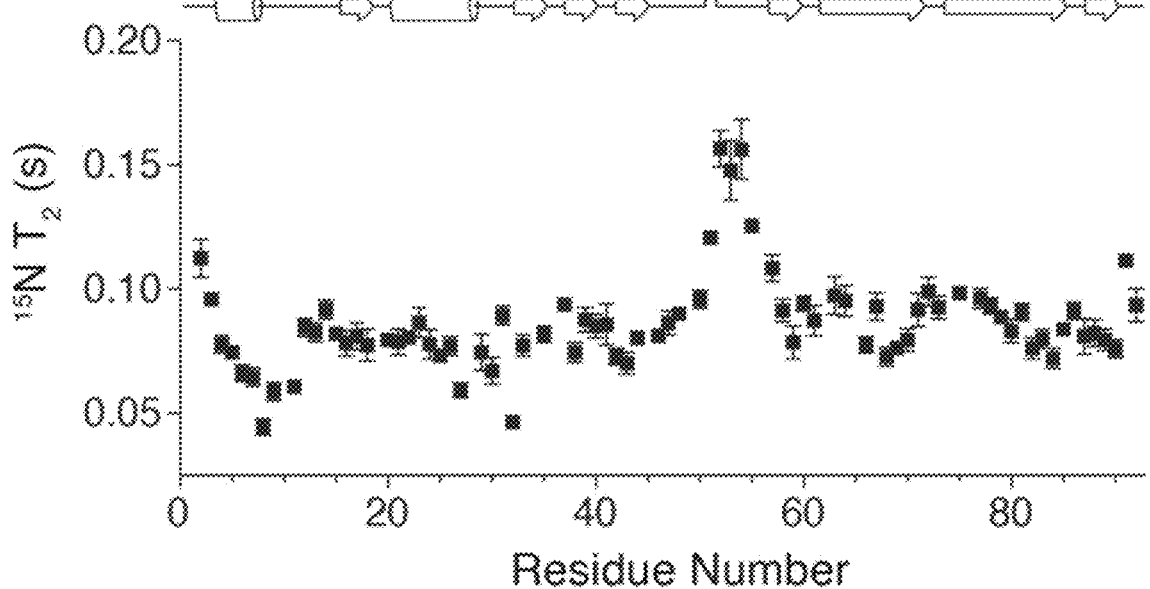
Figure 14:
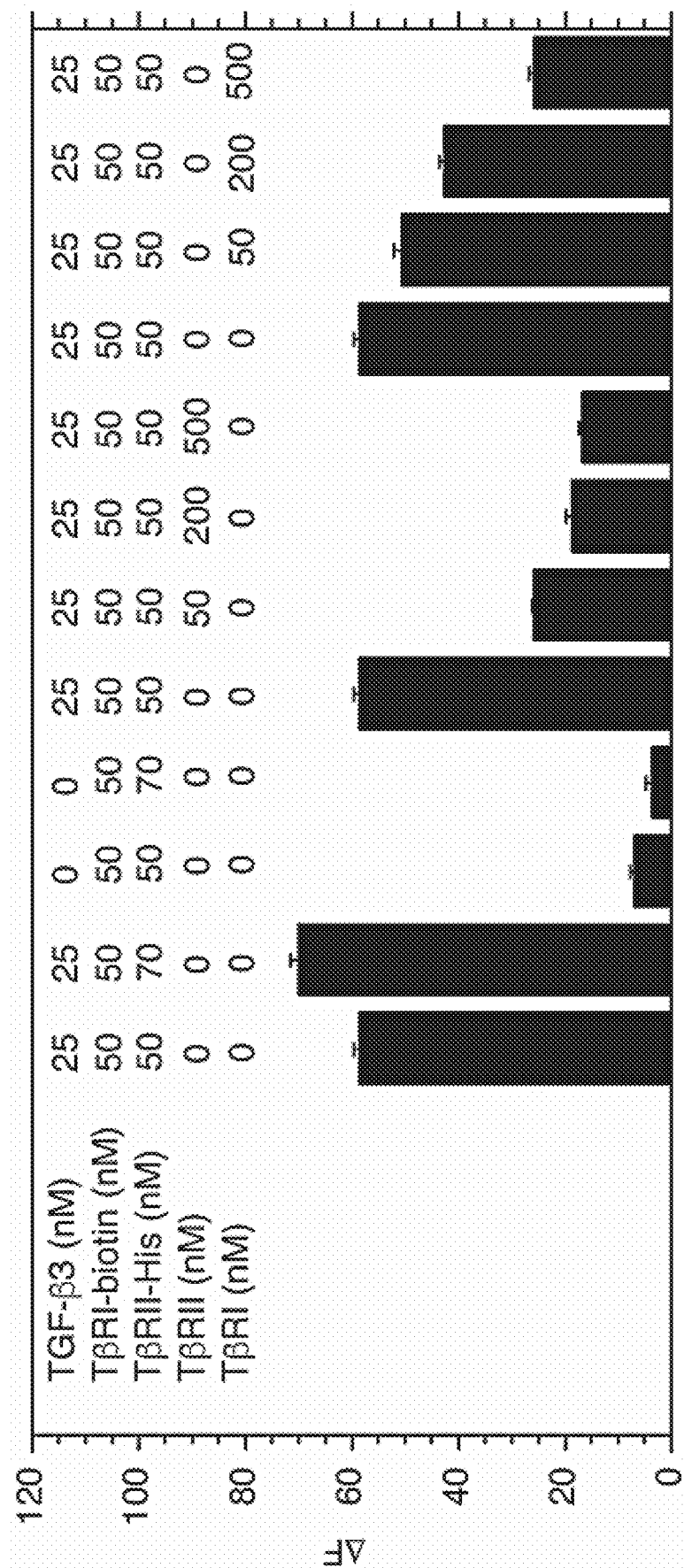
FIG. 14: TR-FRET assay for assessing TGF-β:TβRII:TβRI complex assembly. The concentration of the terbium-cryptate anti-hexahistidine tag antibody donor fluorophore and streptavidin-665 acceptor fluorophore was 2 nM and 30 nM, respectively.

Human embryonic kidney 293 (HEK293) cells stably transfected with the CAGA$_{12}$ TGF-β reporter were used for the luciferase reporter assays (Thies et al., *Growth Factors* 18:251-259, 2001). HEK293 cells containing the stably transfected CAGA$_{12}$ TGF-β reporter were maintained in Dulbecco's modified eagles medium (DMEM) containing 10% fetal bovine serum (FBS) and 1% penicillin/streptomycin. Cells were treated for 16 hours with a TGF-β (TGF-β1, mTGF-β3 or mmTGF-β2-7M) concentration series or an mmTGF-β2-7M concentration series in the Time-Resolved FRET Assays The following purified proteins were used to address the ligand requirements for the formation of complexes containing TβRI and TβRII: TGF-β3, mTGF-β3, mmTGF-β2-7M, biotinylated TβRI-ΔC-Avi and TβRII-His. Initially 20 µM binary complexes of TGF-β3:TbRII-His (1:2), mTGF-β3:TβRII-His (1:1), and mmTGF-β2-7M:TβRII-His (1:1) were formed in a 50 mM Tris, pH 7.5 buffer and stored at 4° C. A time-resolved fluorescence resonance energy transfer (TR-FRET) assay based on the proximity-dependent transfer of fluorescence from the donor terbium cryptate labeled anti-His mAb (Tb-anti-His, CisBio, Bedford, MA) to the acceptor XL665 labeled streptavidin (SA-665, CisBio, Bedford, MA) was used to monitor the assembly of ternary ligand:TβRII-His:biotinylated TβRI-ΔC-Avi complexes. Fifty μL assays containing 100 nM or 250 nM TGF-β3:TβRII-His (1:2), mTGF-β3:TβRII-His (1:1), and mmTGF-β2-7M:TβRII-His (1:1) complexes were incubated with 50 nM biotinylated TβRI-ΔC-Avi. Each 50 μl ternary complex formation assay also contained 2 nM Tb-anti-His and 30 nM SA-665 and was incubated at room temperature for 2 hours. Each condition was tested in replicates of six. Buffer control (n=6) contained only 2 nM Tb-anti-His and 30 nM SA-XL665. The buffer conditions for each assay were 50 mM Tris, 50 mM NaCl, pH 7.5. The assays were performed in Corning black 384 well low flange microplates (ThermoFisher, Waltham, MA). After a 2-hour incubation, the assay plate was measured for terbium/XL-665 TR-FRET on a BMG Labtech Pherastar FS multimode plate reader (BMG Labtech Inc., Cary, NC). An optic module containing 337, 490 and 665 nm filters was used to monitor TR-FRET producing raw data for 337/490 (terbium emission) and 337/665 (XL-665) emission. The ratio of 665 emission/490 emission was determined for each condition and was subsequently used to calculate ΔF, which is a measure that reflects the signal of the sample versus the background. ΔF was calculated using the following equation: (Ratio$_{signal}$−Ratio$_{negative}$/Ratio$_{negative}$)×100. The Ratio$_{signal}$ refers to the assays containing the trimeric complexes or buffer control. The Ratio$_{negative}$ refers to two assays buffer control (2 nM Tb-anti-His and 30 nM SA-665). For the buffer control, 2 out of the 6 replicates were assigned as negative controls for the purpose of calculating ΔF. ΔF was calculated for the remaining 4 buffer control replicates. Results are shown in FIGS. 7A, 7B and 14.

Analytical Ultracentrifugation mTGF-β3, mmTGF-β2, and mmTGF-β2-7M were analyzed by sedimentation velocity to establish equilibrium constants for self-association of monomeric TGF-βs to form homodimers. mTGF-β3, mmTGF-β2, and mmTGF-β2-7M were each measured at 280 nm in an epon two channel centerpiece fitted with quartz windows, and centrifuged at 20° C. and 42,000 rpm for 27 hours in a 15 mM sodium phosphate buffer adjusted to pH 3.8, containing 100 mM NaCl. Three hundred scans were collected in intensity mode on a Beckman Optima XL-I analytical ultracentrifuge at the CAUMA facility at the UTHSCSA. Data analysis was performed with UltraScan release 2130 (Demeler and Gorbet, Analytical ultracentrifugation data analysis with Ultrascan-III, In *Analytical Ultracentrifugation: Instrumentation, Software, and Applications* (Uchiyama, S., Stafford, W., and Laue, T., Eds.), pp 119-143, Springer, 2016; Demeler et al., A comprehensive data analysis package for analytical ultracentrifugation experiments, 2016), calculations were performed at the Texas Advanced Computing Center on Lonestar-5. The sedimentation velocity data were initially fitted with the two-dimensional spectrum analysis as described in (Demeler, *Curr Protoc Protein Sci Chapter* 7, Unit 7 13, 2010) to remove time- and radially invariant noise from the raw data, and to fit the meniscus position. Subsequently, the data were fitted to a discrete monomer-dimer model using the adaptive space-time finite element method (Cao and Demeler, *Biophys J* 95, 54-65, 2008) and genetic algorithms for the parameter optimization (Demeler et al., *Macromol Biosci* 10, 775-782, 2010). The monomer-dimer model accounts for mass action and the reversible association behavior, fitting the K$_D$, hydrodynamic parameters, as well as the partial specific volume while assuming the predicted molar mass for either wildtype or mutant. A Monte Carlo analysis (Demeler and Brookes, *Colloid Polym Sci* 286, 129-137, 2008) with 100 iterations was performed for each dataset to obtain fitting statistics. Buffer density and viscosity were estimated with UltraScan based on buffer composition and all hydrodynamic values were corrected for standard conditions (20° C. and water). The fitting results provided an excellent fit with random residuals and very low RMSD values. All results are summarized in Table 4, and FIGS. 11-13.

TABLE 4

Fitting results for the finite element monomer-dimer model for TGF-β monomers

| Parameter | mTGF-β3 | mmTGF-β2 | mmTGF-β2-7M |
|---|---|---|---|
| RMSD of the fit (OD$_{280}$ nm) | 0.00253 | 0.00276 | 0.00564 |
| K$_{D1-2}$ (M) | $4.1 \times 10^{-6}$ | $4.4 \times 10^{-5}$ | $5.6 \times 10^{-5}$ |
| | ($1.9 \times 10^{-6}$, | ($3.9 \times 10^{-5}$, | ($5.3 \times 10^{-5}$, |
| | $6.2 \times 10^{-6}$) | $4.8 \times 10^{-5}$) | $6.0 \times 10^{-5}$) |
| k$_{off}$(1/s) | $1.3 \times 10^{-6}$ | $2.6 \times 10^{-5}$ | $2.5 \times 10^{-5}$ |
| | ($9.2 \times 10^{-7}$, | ($2.0 \times 10^{-5}$, | ($1.9 \times 10^{-5}$, |
| | $1.7 \times 10^{-6}$) | $3.1 \times 10^{-5}$) | $3.0 \times 10^{-5}$) |
| Loading concentration (M) | $1.25 \times 10^{-5}$ | $1.58 \times 10^{-5}$ | $4.50 \times 10^{-5}$ |
| Frictional coefficient, monomer | 1.04 (1.00, 1.10) | 1.18 (1.16, 1.19) | 1.31 (1.29, 1.33) |
| Frictional coefficient, dimer | 1.37 (1.30, 1.45) | 1.30 (1.29, 1.31) | 1.43 (1.42, 1.45) |
| Sedimentation coefficient, monomer (s, ×10$^{-13}$) | 1.29 (1.26, 1.32) | 1.24 (1.23, 1.25) | 1.48 (1.47, 1.49) |
| Sedimentation coefficient, dimer (s, ×10$^{-13}$) | 1.56 (1.54, 1.58) | 1.78 (1.75, 1.81) | 2.15 (2.14, 2.17) |

*Parameters in parenthesis denote the 95% confidence interval obtained from Monte Carlo analysis Results Design of Engineered Mini-Monomeric TGF-β (mmTGF-β)

The structures of the TGF-β receptor complexes (Groppe et al., *Mol Cell* 29, 157-168, 2008; Radaev et al., *J Biol Chem* 285:14806-14814, 2010), as well as accompanying binding and cross-linking studies with TGF-β3 C77S (Thiliga et al., *J Mol Biol* 354, 1052-1068, 2005; Groppe et al., *Mol Cell* 29, 157-168, 2008; Huang et al., *EMBO J* 30:1263-1276, 2011), suggested that the signaling capacity of monomeric TGFβs (TGF-β1 C77S or mTGF-β1 and TGF-β3 C77S or mTGF-β3) arise from their ability to non-covalently dimerize and in turn bind their receptors (FIGS. 1A and 1C). This led to the hypothesis that it should be possible to diminish or completely eliminate receptor complex assembly with monomeric TGF-βs by removing or altering residues responsible for dimer formation and binding of TβRI. The structural motif that likely contributes the greatest to self-association of the monomers is the "heel" α-helix, α-helix 3 (FIG. 1A). This helix is highly amphipathic and has numerous hydrophobic interactions with residues that line the "palm" of the opposing monomer (FIG. 1B). This helix also forms a large portion of the binding surface for TβRI (FIG. 1C). Thus, it was hypothesized that elimination of α-helix 3 would interfere with both self-association of the monomers and binding of TβRI, but would not impair TβRII binding as this occurs through the ligand fingertips far away from α-helix 3 (FIG. 1A).

To evaluate this hypothesis, bacterial expression constructs were generated for TGF-β1, TGF-β2, and TGF-β3 in which residues 52-71 were eliminated and Cys-77 was substituted with serine. This corresponds to deletion of all of α-helix 3, as well as five flanking residues on the N-terminal end and three flanking residues on the C-terminal end (FIG. 1D). The length of the deletion was chosen so as to leave a sufficient number of residues between the last residue of β-strand 4 (Gly-48) and the first residue of β-strand 5 (Cys-77/Ser-77) to form an unconstrained loop that bridges β-strands 4 and 5. Although a secondary consideration, either two (TGF-β2) or three (TGF-β1 and -β3) of the loop-forming residues were also substituted to increase the net overall charge at pH 7.0 for the full-length TGF-β1, -β2, and -β3 monomers from −0.9, +1.1, and +4.4 to −3.1, +3.9, and +6.1, respectively, for the constructs in which α-helix 3 was deleted (FIG. 1D). The rationale for this was that the solubility of the monomers, which like the homodimers are poor from pH 4.5 to 9.5 (see FIGS. 4A and 4B), might be improved by both removing hydrophobic α-helix 3 and by artificially increasing the net charge at pH 7.0.

Isolation and Physical Characterization of mmTGF-β2

The TGF-β1, -β2, and -β3 "mini-monomers" described above, designated mmTGF-β1, mmTGF-β2, and mmTGF-β3, were expressed in *Escherichia coli* and accumulated in the form of insoluble inclusion bodies. The inclusion bodies were isolated, and after reconstitution and purification in denaturant, the mini-monomers were renatured by dilution into CHAPS-containing buffer at pH 9.0 as described previously (Huang et al., *Methods Mol Biol* 1344:63-92, 2016). The folding of the mini-monomers differed greatly; a large portion of the mmTGF-β2 remained soluble during the folding and yielded large amounts of monomeric protein after purification by cation exchange chromatography, whereas only a small amount of mmTGF-β1 and mmTGF-β3 remained soluble during the folding, and either no monomeric protein (TGF-β1) or a very small amount of monomeric protein (TGF-β3) was obtained after purification by cation exchange chromatography. This pattern mirrors the pattern previously observed for the folding of TGF-β homodimers from full-length wild type monomers (Huang et al., *Methods Mol Biol* 1344:63-92, 2016) and likely reflects differences in the intrinsic propensity of the monomers to properly form the four intramolecular disulfides characteristic of each monomer. mmTGF-β2 was the least desired variant, due to the expected low affinity for binding TβRII. However, this was considered an addressable concern based on prior studies, which demonstrated that substitution of Lys-25, Ile-92, and Lys-94 in TGF-β2 with the corresponding residues in TGF-β1 and TGF-β3 engendered TGF-β2 with the ability to bind TβRII with high affinity (Baardsnes et al., *Biochemistry* 48:2146-2155, 2009; De Crescenzo et al., *J Mol Biol* 355:47-62, 2006). To determine whether mmTGF-β2 was suitable for further development in the manner described above, it was characterized in terms of its folding, solubility, and receptor binding properties. To assess folding, a $^{15}N$-labeled sample of mmTGF-β2 was prepared and examined by recording a two-dimensional $^{1}H$-$^{15}N$ shift correlation spectrum (FIG. 2A). This revealed a highly dispersed spectrum characteristic of natively folded protein. The spectrum could be fully assigned, and analysis of the assigned chemical shifts to identify secondary structure propensities showed that the protein had the expected secondary structure, particularly in the palm region formed by the cysteine knot and the finger region where TβRII binds (FIG. 9A). This analysis further showed that the newly created loop between residues 47 and 56 had near zero probability of forming either an α-helix or β-strand, suggesting that it is likely flexible as would be expected for a loop of this length connecting two antiparallel β-strands. This was directly confirmed by an analysis of backbone $^{15}N$ $T_2$ values. These values provide information about motions on fast (nanosecond-picosecond) and intermediate (microsecond-millisecond) time scales and were significantly elevated in the region corresponding to the newly created loop relative to the other parts of the protein (FIG. 9B), which, except for the N terminus and the short loop connecting α-helix 1 and β-strand 1, are expected to be structurally well-ordered.

To directly examine the three-dimensional structure, mmTGF-β2 was crystallized, and its structure was determined to a resolution of 1.8 Å using molecular replacement (Table 3). The overall fold of mmTGF-β2 was shown to be highly similar to that previously determined for TGF-β2, with the exception of the newly created loop, which was shown to take the place of α-helix 3 as anticipated (FIG. 2B). Superimposition of the mmTGF-β2 with the monomer from the structure of TGF-β2 shows that there is a systematic displacement of up to about 1.5 Å of the finger region of mmTGF-β2 relative to TGF-β2. Such differences appear to be the result of bending of the monomer near the center of the finger region and not a change in the structure of the finger region, as superimposition of the fingers alone show that they correspond closely, with a backbone root-mean-square deviation of under 0.2 Å and similar orientations of the side chains of several residues that pack and stabilize the fingers (FIG. 2D). Such bending is also supported by an overlay of the two molecules of mmTGF-β2 present in the crystallographic asymmetric unit, which also exhibit a smaller but still noticeable displacement of the finger regions relative to one another (FIG. 2C). Consistent with the NMR analysis, not only was the electron density noticeably weaker in the region corresponding to the newly created loop, but also it was shown to adopt different orientations for the two molecules from the asymmetric unit FIG. 2C).

The similar folding of mmTGF-β2 relative to TGF-β2, especially in the TβRII-binding finger region, suggested that it would also bind TβRII in a similar manner. To evaluate this, surface plasmon resonance (SPR) experiments were performed in which the same concentration series of TβRII was injected over TGF-β2 and mmTGF-β2 immobilized on separate flow cells (FIGS. 3A and 3B). Although it was not possible to quantitate affinity due to weak binding, the sensorgrams nonetheless showed similar shapes and concentration dependence. These sensorgrams showed that mmTGF-β2 binds TβRII weakly, consistent with earlier reports Baardsnes et al., *Biochemistry* 48:2146-2155, 2009), and that it did so in a manner qualitatively similar to TGF-β2.

The solubility of mmTGF-β2 appeared to be significantly better than that of TGF-β2 and the full-length TGF-β2 monomer, mTGF-β2, as samples of the former could be readily prepared at concentrations of 2-3 mg ml$^{-1}$ without noticeable precipitation at pH 7.0, whereas samples of the latter two proteins were completely precipitated under these same conditions. To quantitate solubility, TGF-β2, mTGF-β2, and mmTGF-β2 were prepared as concentrated stocks in 100 mM acetic acid, pH 2.9, where they were readily soluble and then diluted into PBS, pH 7.4. The light scattering at 340 nM was measured to assess precipitation, and then the samples were centrifuged, and the absorbance at 280 nM was measured to assess the protein concentration. This demonstrated that TGF-β2 and mTGF-β2 were both effectively insoluble at neutral pH over the entire concentration range evaluated (7-100 µM) (FIGS. 4A and 4B). This is consistent with the known poor solubility of the TGF-β homodimers (Pellaud et al., *J Biol Chem* 274:7699-7704, 1999), but it shows that this property also extends to full-length monomeric TGF-βs. The mini-monomeric TGF-β2 (mmTGF-β2) in contrast, exhibited modest light scattering and a corresponding modest reduction in the amount of soluble protein relative to that expected when the protein concentration was 40 µM or higher, indicating that indeed mmTGF-β2 was reasonably soluble at neutral pH, although not perfectly so. This was reflected in NMR spectra, which showed that although 100-200 µM $^{15}$N mmTGF-β2 samples could be readily prepared, the spectrum was nonetheless poor, with the only detectable signals arising from residues in the flexible parts of the protein, namely the N terminus, the exposed loop between α-helix 1 and β-strand 1, and the newly created loop between β-strands 4 and 5. The fact that signals could only be detected from the flexible parts of the protein suggested that mmTGF-β2 forms large soluble aggregates under these conditions. Through trial and error, it was found that these soluble aggregates could be eliminated by addition of the zwitterionic detergent CHAPS, with the majority of the NMR signals appearing at the concentration of 5 mM CHAPS and all of the NMR signals appearing at 10 mM CHAPS. Thus, all NMR spectra, including that shown in FIG. 2A, were recorded in the presence of 10 mM CHAPS.

Isolation and Physical Characterization of mmTGF-β2-7M

Figure 5A:
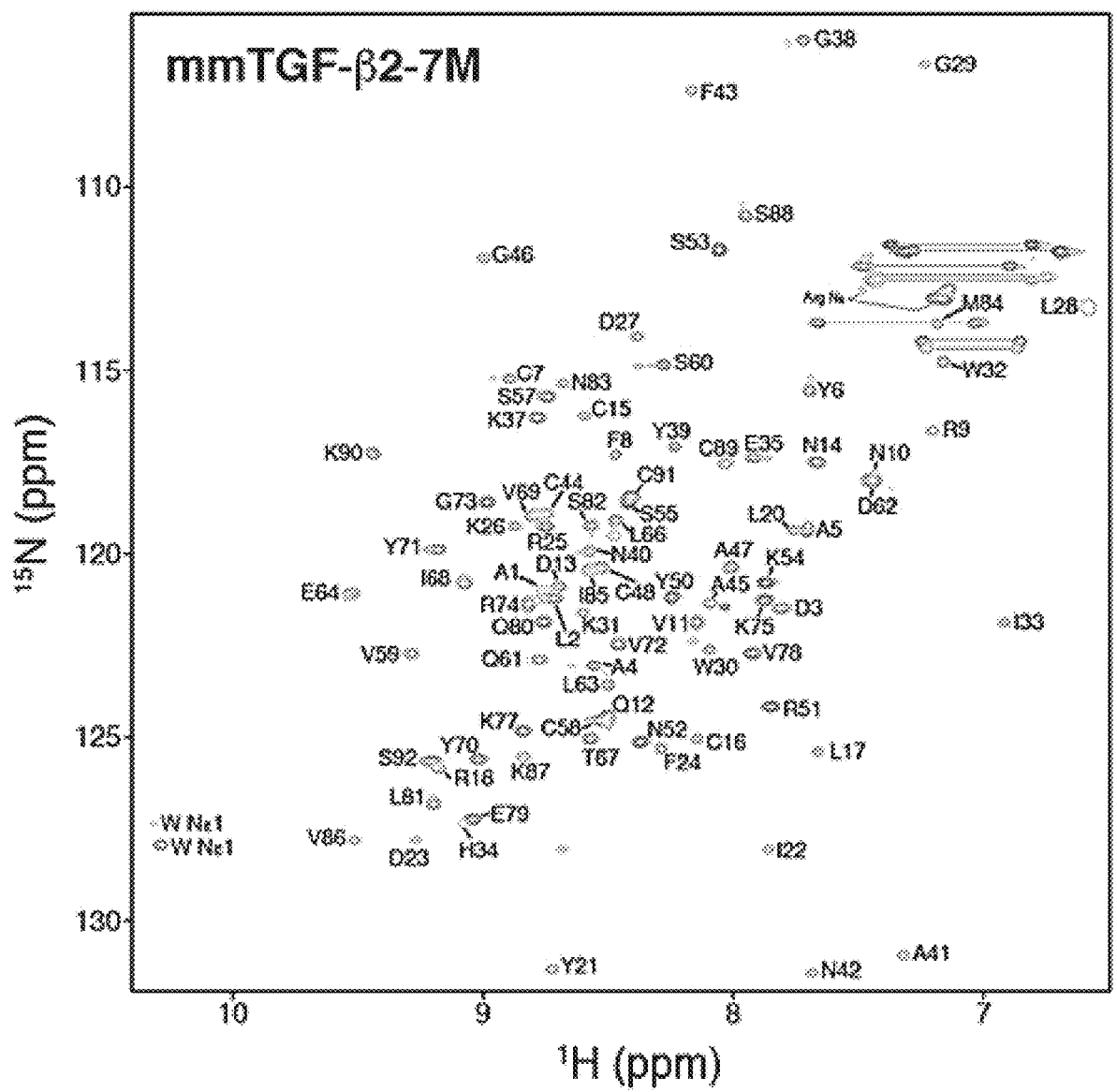
Figure 5B:
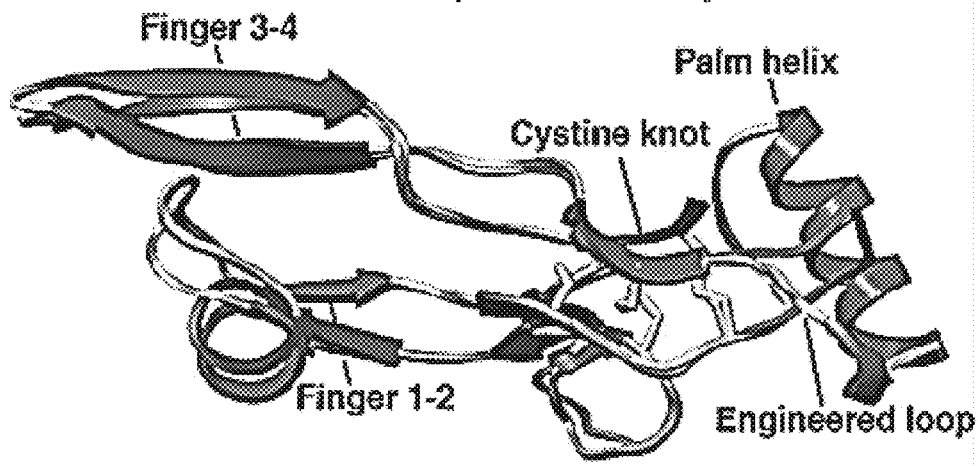
Figure 5C:
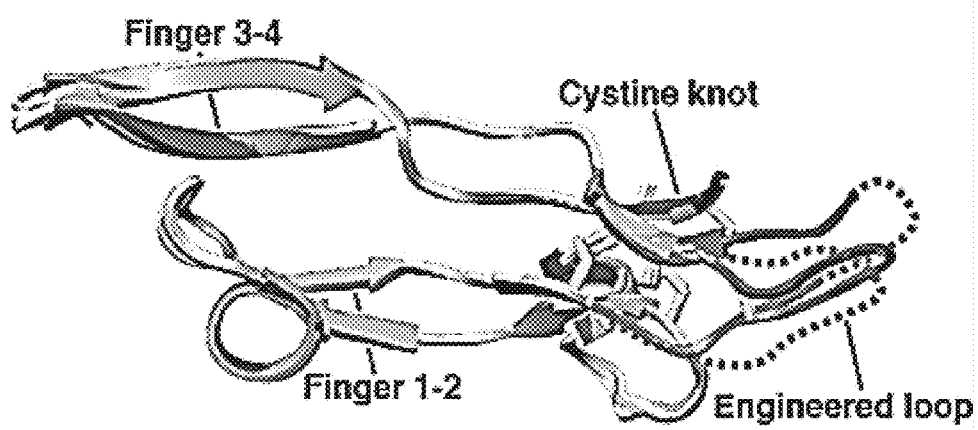
Figure 5E:
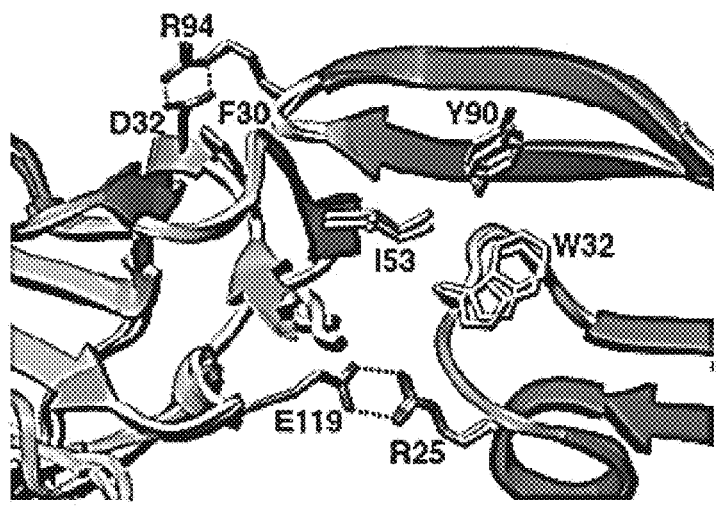
Figure 5D:
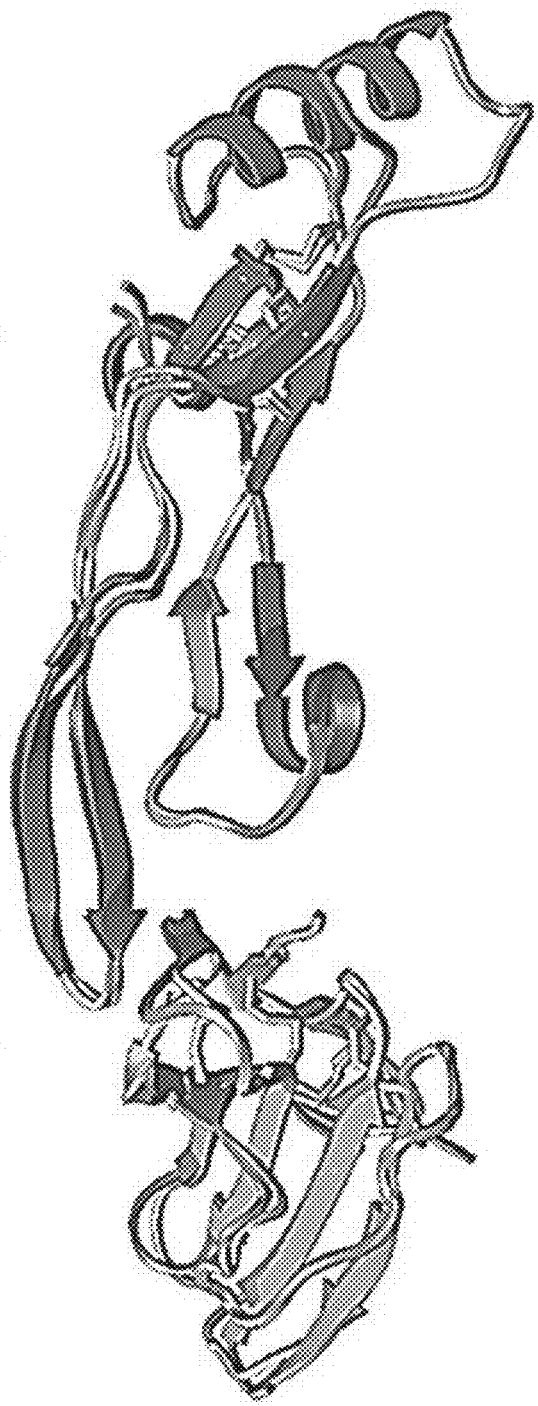
Figure 11:
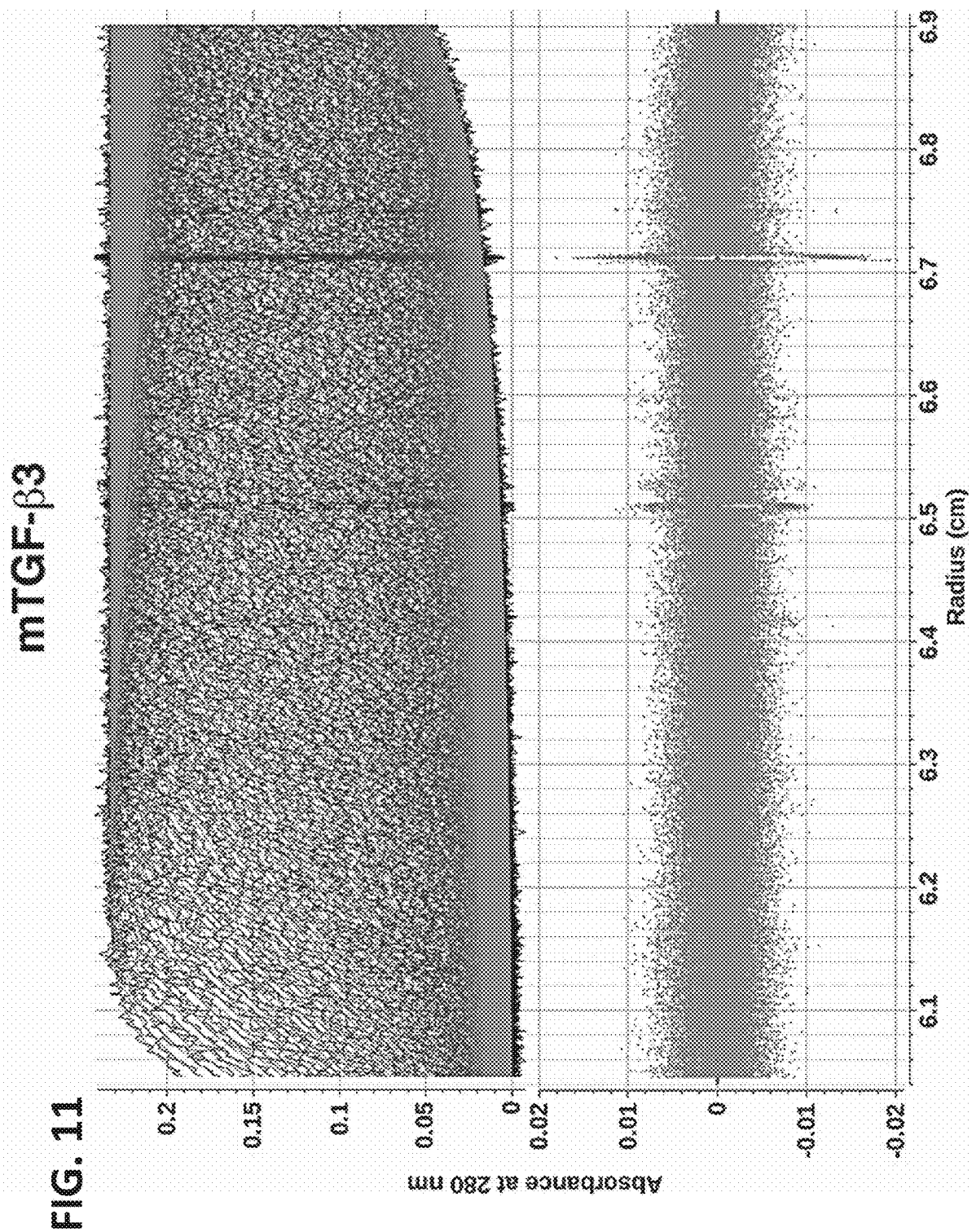
FIG. 11: Finite element fit of a reversible monomer-dimer model to the sedimentation velocity experiment of mTGF-β3. Experimental data with finite element fit overlayed shown on top, residuals are shown on the bottom.
Figure 12:
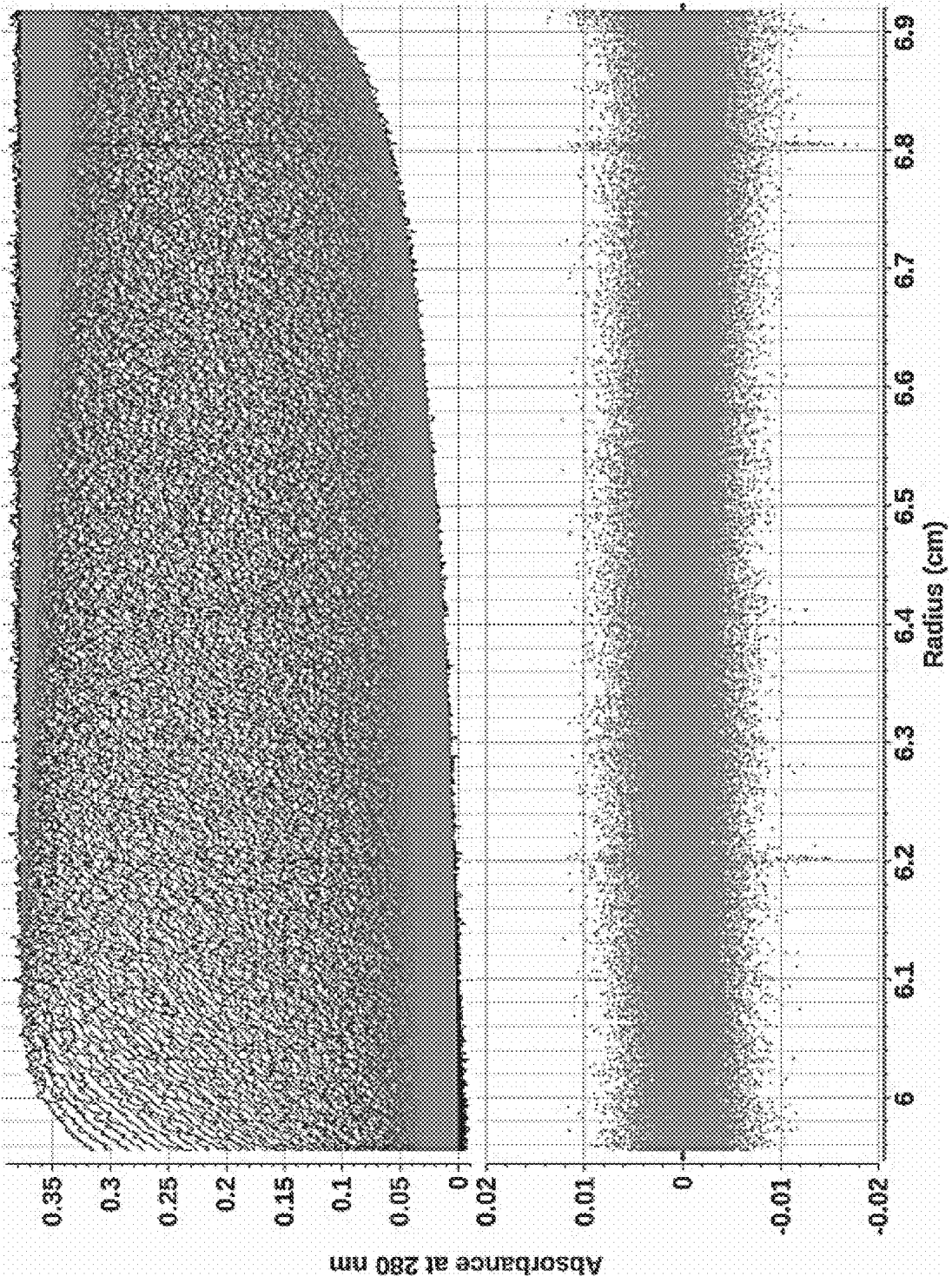
FIG. 12: Finite element fit of a reversible monomer-dimer model to the sedimentation velocity experiment of mmTGF-β2. Experimental data with finite element fit overlayed shown on top, residuals are shown on the bottom.
Figure 13:
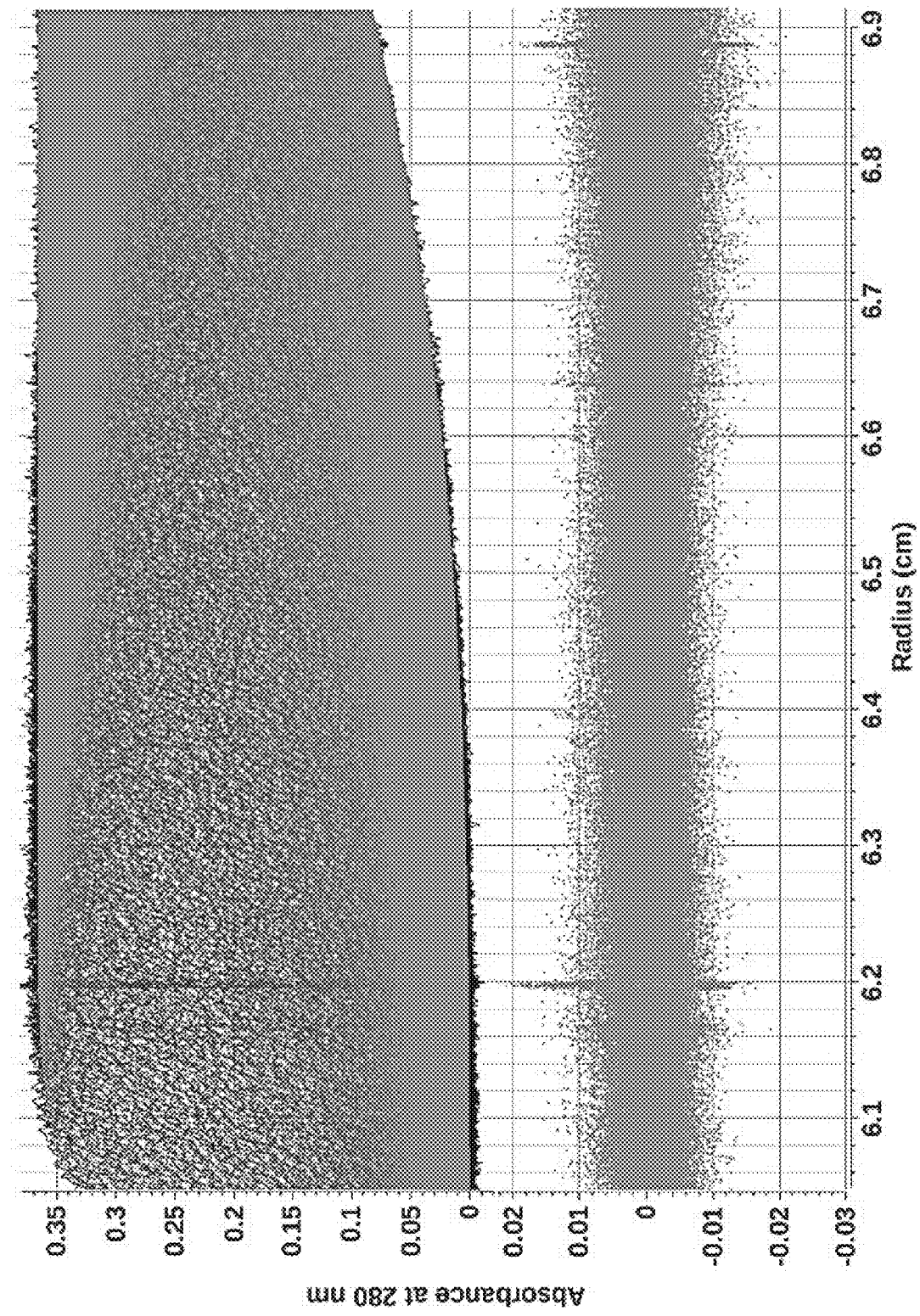
FIG. 13: Finite element fit of a reversible monomer-dimer model to the sedimentation velocity experiment of mmTGF-β2-7M. Experimental data with finite element fit overlayed shown on top, residuals are shown on the bottom.

The results presented above show that whereas mmTGF-β2 is natively folded, it nonetheless possesses low intrinsic affinity for binding TβRII. To confer mmTGF-β2 with the ability to bind TβRII with high affinity comparable with that of TGF-β1 and TGF-β3, the three residues in mouse TGF-β2 shown previously to differ in the interface with TβRII, Lys-25, Ile-92, and Asn-94 (De Crescenzo et al., *J Mol Biol* 355:47-62, 2006; Hart et al., *Nat Struct Biol* 9:203-208, 2002), were substituted with the corresponding residues from TGF-β1 and -β3, Arg-25, Val-92, and Arg-94 (FIGS. 1E and 1F). In previous studies, substitution of these three residues was shown to be sufficient to confer TGF-β2 with a TβRII binding affinity comparable with TGF-β1 and TGF-β3 (Baardsnes et al., *Biochemistry* 48:2146-2155, 2009; De Crescenzo et al., *J Mol Biol* 355:47-62, 2006). Despite this, four additional residues peripheral to the TβRII-binding site that differed in TGF-β2 relative to TGF-β1 were also substituted with the corresponding residues from TGF-β1 (R26K, L89V, T95K, and I98V) (FIGS. 1E and 1F). Although previous results suggested this was not strictly necessary, it was nonetheless done to ensure that the precise orientation of residues in the mmTGF-β2-binding site for TβRII matched as closely as possible with that in the high affinity TGF-β isoforms, TGF-β1 and TGF-β3. The resulting construct bearing these seven amino acid substitutions, designated mmTGF-β2-7M (FIG. 1E, FIG. 9 and Table 1), was expressed in *E. coli* in the form of insoluble inclusion bodies. As with mmTGF-β2, most of the protein remained in solution after reconstitution and dilution into native folding buffer, and large amounts of homogenous monomer could be isolated (4-5 mg/liter of *E. coli* culture medium).

The folding and homogeneity of the isolated mmTGF-β2-7M was evaluated by NMR, and as with mmTGF-β2, the protein was found to have the expected number of signals in a 2D $^1H$-$^{15}N$ shift correlation spectrum (FIG. 5A) as well as secondary structure, as determined by an analysis of the NMR secondary shifts (FIG. 10A). The solubility of mmTGF-β2-7M was evaluated as before, and as shown, its behavior was comparable or perhaps slightly better than that of mmTGF-β2 (FIGS. 4C and 4D). This slight improvement in the macroscopic solubility did not however change the microscopic solubility as NMR analysis showed that it was still necessary to include 10 mM CHAPS in the sample buffer to detect signals from all of the backbone amide resonances in the protein.

The three-dimensional structure of mmTGF-β2-7M was determined by crystallography to a resolution of 2.75 Å (Table 3), and as before the overall fold was preserved relative to TGF-β2, with the only difference being a slight hinge bending of the monomer as described for mmTGF-β2 (FIGS. 5B and 5C). The increase in the $^{15}N$ $T_2$ relaxation times in the region corresponding to the newly formed loop in mmTGF-β2-7M was comparable with that in mmTGF-β2 (FIG. 10B). This suggested that the missing density in the region corresponding to the newly formed loop in mmTGF-β2-7M, which among the three molecules in the asymmetric unit was observed for part of chain A and most of chain C, was not due to increased dynamics, but other factors, most likely the lower resolution of the mmTGF-β2-7M structure compared with the mmTGF-β2 structure (Table 3).

To determine whether mmTGF-β2-7M bound TβRII with high affinity, variants of mmTGF-β2-7M and TGF-β3 were produced bearing an N-terminal avitag, and after biotinylation and immobilization onto a streptavidin-coated SPR sensor, their binding affinity for TβRII was measured by performing kinetic SPR experiments (FIGS. 3C and 3D). The sensorgrams obtained differed greatly from that previously obtained for mmTGF-β2 and TGF-β2, in that they exhibited a clear pattern of saturation. The sensorgrams were furthermore shown to have similar shapes as well as fitted parameters, including $K_D$ values (Table 2), which were within experimental error of one another and consistent, although on the high end, with $K_D$ values reported earlier for TβRII binding to TGF-β1 and TGF-β3 (Huang et al., *EMBO J* 30:1263-1276, 2011; Baardsnes et al., *Biochemistry* 48:2146-2155, 2009; De Crescenzo et al., *J Mol Biol* 355:47-62, 2006).

To determine whether the interactions that enabled high affinity TβRII binding were preserved in mmTGF-β2-7M compared with TGF-β1 and TGF-β3, the mmTGF-β2-7M•TβRII complex was crystallized, and its structure was determined to a resolution of 1.88 Å (Table 3). The overall structure of the mmTGF-β2-7M•TβRII complex was shown to be very similar to that of one of the TβRII-bound monomers from the structure of the TGF-β3-TβRII•TβRI complex, with TβRII bound to the mmTGF-β2-7M fingertips in a manner that is essentially indistinguishable from that of TGF-β3 (FIG. 5D). The interactions known to contribute most significantly to high affinity binding are furthermore shown to be fully preserved in the mmTGF-β2-7M•TβRII complex relative to TGF-β1•TβRII and TGF-β3•TβRII complexes that have been previously determined (the TGF-β3•TβRII complex determined to 1.8 Å (Hart et al., *Nat Struct Biol* 9:203-208, 2002) is shown as this is the highest resolution structure determined to date) (FIG. 5E). This includes the packing of Ile-53 from TβRII in the hydrophobic pocket between the TGF-β fingers, and the hydrogen-bonded ion pairs formed between TGF-β Arg-25 and Arg-94 on the tips of the loops connecting fingers 1/2 and 3/4, respectively, and the carboxylate groups of Glu-119 and Asp-32 on TβRII (FIG. 5E).

Inhibitory Activity of mmTGF-β2-7M and the Underlying Mechanism

The results presented above show that mmTGF-β2-7M possesses one of the essential attributes required to function as a dominant negative inhibitor of TGF-β signaling, which is the ability to bind TβRII with high affinity comparable with that of TGF-β1 and TGF-β3. To directly assess whether mmTGF-β2-7M might signal and, if not, whether it might function as an inhibitor, TGF-β signaling was assessed by treating HEK293 cells stably transfected with a TGF-β luciferase reporter under the control of a $CAGA_{12}$ promoter (Thies et al., *Growth Factors* 18:251-259, 2001) with increasing concentrations of TGF-βs. The results showed that dimeric TGF-β1 (TGF-β1) and full-length monomeric TGF-β3 (mTGF-β3) resulted in a sigmoidal increase in the luciferase response, with concentrations of roughly 25 pM TGF-β1 and 250 pM mTGF-β3 leading to no further increase in the measured luciferase response. This is consistent with earlier reports that showed that (full-length) monomeric TGF-β1 and -β3 were 5-15-fold less potent than their dimeric counterparts (Zúñiga et al., *J Mol Biol* 354, 1052-1068, 2005; Amatayakul-Chantler et al., *J Biol Chem* 269:27687-27691, 1994). The normalized luciferase responses could be readily fitted to a standard model for ligand-dependent activation and yielded $EC_{50}$ values of 12.4±1.5 pM for TGF-β1 and 182±16 pM for mTGF-β3. The values for TGF-β1 and mTGF-β3 were in close accord with the values previously reported by Amatayakul-Chantler et al. (*J Biol Chem* 269:27687-27691, 1994) for TGF-β1 and by Zúñiga et al. (*J Mol Biol* 354, 1052-1068, 2005) for mTGF-β3. The potent sub-nanomolar signaling activity observed for TGF-β1 and mTGF-β3 stands in contrast to that of mmTGF-β2-7M, which had no detectable signaling activity at the concentration that led to a saturating response for mTGF-β3 (ca. 200 pM) or at concentrations that were up to four orders of magnitude higher (FIG. 6A). Thus, mmTGF-β2-7M was either completely devoid of signaling activity or it possessed signaling activity, but with a potency more than a 10,000-fold less than that of mTGF-β3.

To further investigate the properties of mmTGF-β2-7M, a competition experiment was performed in which the same HEK293 luciferase reporter cell line was stimulated with a constant sub-$EC_{50}$ concentration of dimeric TGF-β1 (8.0 pM) and increasing concentrations of mTGF-β3 or mmTGF-β2-7M. The results showed that mTGF-β3 further stimulated signaling with a midpoint concentration similar to that of mTGF-β3 alone (FIG. 6B). The fitted $EC_{50}$ values confirm this, with an $EC_{50}$ of 182±16 pM for the data shown in FIG. 6A and $EC_{50}$ of 194±36 pM for the data shown in FIG. 6B. The behavior of mmTGF-β2-7M was very different, with no detectable change in the signaling activity when added up to concentrations of 10 nM, but with a sharp decrease to no detectable signaling activity when the concentration was increased to 100 nM (FIG. 6B). This shows that mmTGF-β2-7M indeed possesses no signaling activity and that it can function to completely block and inhibit TGF-β signaling. The normalized luciferase responses could be readily fitted to a standard model for ligand-dependent inhibition and yielded an $IC_{50}$ value of 68±7 nM. Similar experiments showed that mmTGF-β2-7M also functioned as a potent competitive inhibitor against the other TGF-β isoforms, TGF-β2 and TGF-β3, with measured $IC_{50}$ values (TGF-β2 $IC_{50}$ 19±3 nM and TGF-β3 $IC_{50}$ 21±8 nM) within a factor of 2-3 of that measured for TGF-β1 (FIGS. 15A and 15B). These $IC_{50}$ values are on the lower end of the range of affinities that have been reported for binding of the high affinity TGF-β isoforms to TβRII, including mmTGF-β2-7M reported herein (Table 2). This suggests that mmTGF-β2-7M functions to inhibit TGF-β signaling by binding to and blocking endogenous TβRII. The fact that the measured potency is greater than the greatest affinity previously reported for TGF-β1 and TGF-β3 binding to TβRII (140 nM) (9), suggests that other factors, such as nonspecific association of mmTGF-β2-7M with the plasma membrane, may serve to potentiate its inhibitory activity.

The finding that mmTGF-β2-7M possesses no apparent signaling activity, and functions as a low nanomolar inhibitor of TGF-β signaling, suggests that the elimination of α-helix 3 diminished non-covalent association of the monomers and greatly attenuated or abrogated TβRI binding. To assess this directly, SPR experiments were performed to determine whether mmTGF-β2-7M could recruit TβRI in the presence of TβRII. To accomplish this, increasing concentrations of TβRI and the same concentration series of TβRI in the presence of near-saturating amounts of TβRII (2 μM) were injected over the same TGF-β3 and mmTGF-β2-7M SPR chip surfaces used for the TβRII binding measurements described above. This showed that TβRI alone binding is negligible to both TGF-β3 and mmTGF-β2-7M (FIGS. 3E and 3F), but unlike TGF-β3, TβRII-bound mmTGF-β2-7M is unable to recruit TβRI (FIGS. 3G and 3H). This is consistent with the earlier result reported by Huang et al. (*EMBO J* 30:1263-1276, 2011) that TβRII-bound mTGF-β3 was significantly or completely impaired in terms of its ability to bind and recruit TβRI. This also provides further evidence that TβRII-bound TGF-β monomers are incapable of binding and recruiting TβRI, but because the mmTGF-β2-7M was immobilized on the surface of the sensor, it alone does not provide any insight as to whether mmTGF-β2-7M might be capable of non-covalently dimerizing and binding and recruiting TβRI.

To address these questions directly, two solution-based techniques were used, analytical ultracentrifugation (AUC) and time-resolved fluorescence resonance energy transfer (TR-FRET). The AUC experiments were performed by measuring the total UV absorbance at 280 nm as a function of the radial position and time as mTGF-β3, mmTGF-β2, and mmTGF-β2-7M were sedimented under acidic conditions, pH 3.8, where the monomers are fully soluble. The AUC data revealed parabolically shaped van Holde-Weischet sedimentation coefficient distribution plots for all three monomers, consistent with each undergoing reversible self-association to form a dimer or other higher order oligomer. To determine more precisely which species might be present in solution, the data were fitted to the simplest model possible, a discrete monomer-dimer equilibrium, using finite element analysis. The fitting procedure resulted in near-perfect fits for all three monomers to the simple monomer-dimer model, as shown by (a) the close overlays between the fitted curves (red) with the raw data, after the time and radially-invariant noise was removed (black) and (b) the absence of any systemic deviations in the residuals (FIGS. 11-13). The fitted parameters further showed that $K_D$ for self-association was 1 order of magnitude greater for mTGF-β3 compared with mmTGF-β2 and mmTGF-β2-7M. Thus, the removal of the heel helix, α3, does diminish self-association of the monomers to form dimers, but it does not completely abrogate dimer formation.

TR-FRET was used to assess the ability of dimeric and monomeric TGF-βs to bind and bring TβRI and TβRII together. This was accomplished by generating differentially tagged forms of TβRII and TβRI and in turn binding to these tags with proteins labeled with fluorescent donors and acceptors. TβRII was tagged with a C-terminal His tag and was bound by a terbium cryptate-labeled anti-His monoclonal antibody fluorescent donor, and TβRI was tagged with an N-terminal avitag, which after enzymatic biotinylation was bound to a dye-labeled (XL-665) streptavidin fluorescent acceptor (FIG. 7A). The addition of TGF-β to the tagged receptors brings them together and leads to a large increase in the ΔF value, which is defined as the ratio of the acceptor and donor emission fluorescent intensities. The TR-FRET assay is demonstrated by the data presented in FIG. 14 and was used here to compare the ability of the TGF-β3 full-length monomer, mTGF-β3, and the TGF-β mini-monomer that binds TβRII with high affinity, mmTGF-β2-7M, to bind and bring TβRI and TβRII together. The TR-FRET signal for mTGF-β3 was shown to be comparable with that of TGF-β3, and this did not depend on whether the TGF-β concentration was 100 or 250 nM (FIG. 7B). The TR-FRET signal of mmTGF-β2-7M was, in contrast, within the error limits of the buffer control, and this did not depend on the TGF-β concentration (FIG. 7B). These results demonstrate that under these conditions, mTGF-β3 retains full capacity to assemble a non-covalent dimeric complex with TβRI and TβRII, but under these same conditions, mmTGF-β2-7M has no capacity to do so. These results, together with the AUC results, indicate that the removal of the heel helix had the effects hypothesized; its removal reduced, but did not eliminate, dimer formation, and even though dimers are still formed, they are unable to bind and recruit TβRI.

Discussion

Figure 15B:
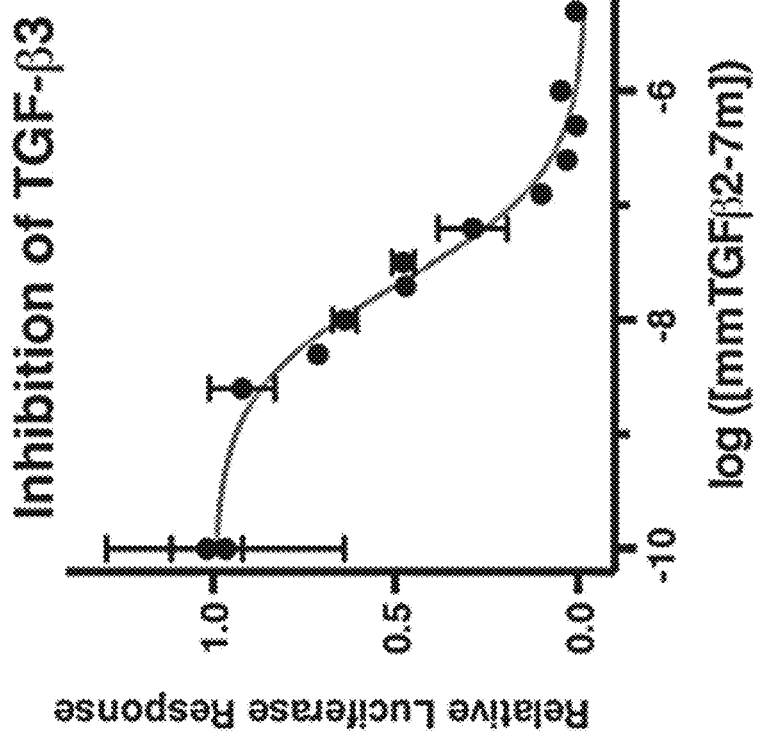
FIGS. 15A-15B: Inhibition of TGF-β2 and TGF-β3 by mmTGF-β2. TGF-β luciferase activity for cells treated with a fixed concentration of TGF-β2 (20 pM.
Figure 15A:
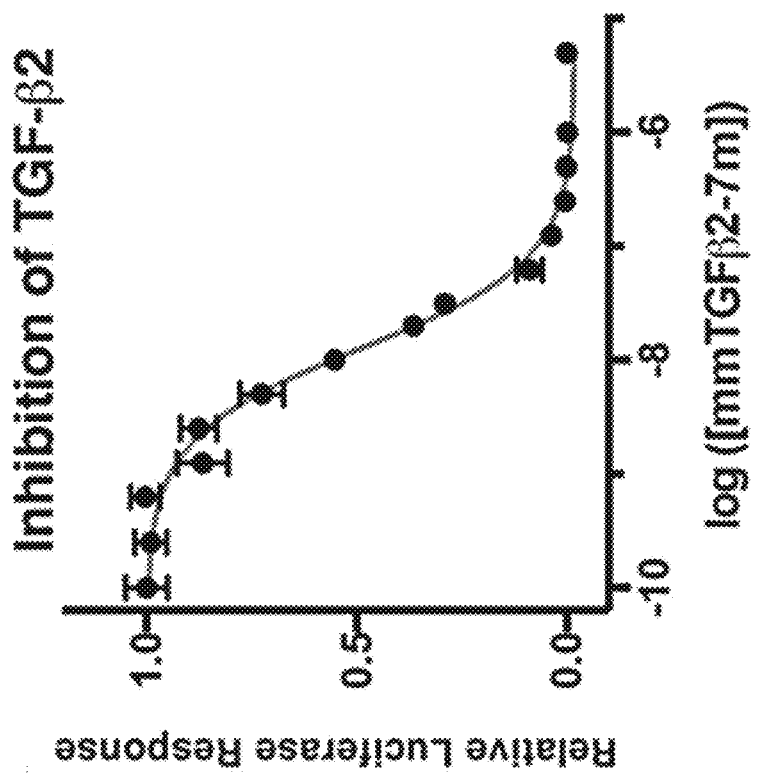

The TGF-βs are responsible for promoting the progression of numerous human diseases (Dietz et al., *Nature* 352:337-339, 1991; Biernacka et al., *Growth Factors* 29:196-202, 2011; Massagué, *Cell* 134:215-230, 2008; Loeys et al., *Pediatr Endocrinol Rev* 10:417-423, 2013), yet despite nearly two decades of preclinical studies and clinical trials, no inhibitors have been approved for use in humans. The results presented herein demonstrate that an engineered TGF-β monomer, lacking Cys-77 and the heel α-helix (α3), functions to potently block and inhibit signaling of the TGF-β1, -β2, and -β3 with $IC_{50}$ values in the range of 20-70 nM (FIG. 6B and FIG. 15). This novel inhibitor has several attributes that overcome limitations that have been encountered with other classes of inhibitors, for example the natural high specificity of TGF-β and thus the inhibitor for TβRII may engender it with much greater specificity, and thus fewer undesirable side effects, compared with the much more promiscuous TGF-β kinase inhibitors. The small size of the inhibitor (~10 kDa) further confers a much greater ability to penetrate tumors and other dense tissues where the TGF-βs drive disease progression, a distinct advantage compared with IgG antibodies, which are much larger (~150 kDa) and tend to occupy only the vascular and interstitial space of well perfused organs (Meibohm (2012) in Therapeutic Proteins: Strategies to Modulate Their Plasma Half-Lives (Kontermann R., editor), pages 23-38, Wiley-Blackwell, Weinheim, Germany; Meibohm and Braeckman (2008), "Pharmacokinetics and Pharmacodynamics of Peptides and Protein Drugs," in Pharmaceutical Biotechnology: Fundamentals and Applications (Crommelin D. J. A., Sindelar R. D., and Meibohm B., eds), pages 95-123, Informa Healthcare, New York). The other advantages of this novel inhibitor include its high intrinsic stability, because of the four intramolecular disulfide bonds that tie the four fingers together, and the fact that it is highly soluble in water at neutral pH, unlike native TGF-β dimers or full-length TGF-β monomers.

The structures of TGF-β receptor complexes, together with the previously published chemical cross-linking data, suggested that the potent signaling activity of TGF-β1 C77S and TGF-β3 C77S was due to the ability of the monomers to non-covalently dimerize and in turn assemble a (TβRI•TβRII)$_2$ heterotetramer. The results presented here, namely the AUC experiments that were used to assess non-covalent dimer formation and the TR-FRET experiments that were used to assess assembly of complexes with TβRI and TβRII, provided further evidence for this. The AUC data showed that full-length monomeric TGF-β3, mTGF-β3, self-associates to form dimers with a dimerization constant of 4.1 μM (Table 4). The TR-FRET data showed that at a concentration of 0.1 or 0.25 μM and in the presence of comparable concentrations of the TβRI and TβRII ectodomains, mTGF-β3 assembles TβRI•TβRII complexes to the same extent as dimeric TGF-β3 (FIG. 7B). That this occurs, even under conditions where the mTGF-β3 concentrations (0.1-0.25 μM, FIG. 7B) were more than an order of magnitude below the $K_D$ value for self-association (4.1 μM, Table 4), indicates that receptor binding also contributes significantly to assembly of TβRI•TβRII complexes. The assembly of TβRI•TβRII complexes with mTGF-β3, and presumably mTGF-β1 as well, therefore appears to be a cooperative process, much like protein folding, in which multiple weaker interactions, including monomer-monomer, non-covalent dimer-receptor, and receptor-receptor interactions, cooperate to enable formation of a thermodynamically stable TGF-β.TβRI•TβRII complex. This manner of cooperative assembly is likely responsible for the ability of mTGF-β1 and mTGF-β3 to induce signaling at concentrations that are more than 4 orders of magnitude below the $K_D$ value for self-association of the monomers ($EC_{50}$ values of about 0.1 nM versus $K_D$ values for self-association of 4.1 μM).

The elimination of the heel helix from the TGF-β monomer was shown to be very effective in terms of blocking the cooperative assembly of TβRI•TβRII complexes as shown by the TR-FRET data (FIG. 7B) and the cell based signaling data (FIGS. 6A and 6B). The AUC data showed that elimination of the heel helix led to the weakening of the monomer-monomer interaction by one order of magnitude (Table 4). The SPR data shown in FIGS. 3G and 3H, further showed that the TβRII-bound form of mmTGF-β2-7M was incapable of binding and recruiting TβRI, which is expected based on published structures of TGF-β receptor complexes that show that TβRI binds to a composite interface formed by both chains of TGF-β, as well as TβRII (Groppe et al., *Mol Cell* 29, 157-168, 2008; Radaev et al., *J Biol Chem* 285:14806-14814, 2010). Thus, the data show that the reduced propensity of the engineered monomer to self-associate, together with what would be expected to be very weak binding of TβRI to any dimers that do form, is responsible for the inability of mmTGF-β2-7M to assemble a TβRI•TβRII complex. This accounts for the lack of signaling activity, and this together with the retention of high affinity TβRII binding accounts for the inhibitory activity.

The other type II receptors of the family, activin type II receptor II, activin type IIB receptor, BMP type II receptor, and anti-Müllerian hormone type II receptor, have either been shown or are predicted to bind the GF knuckle and not the GF fingertips, as does TβRII (Hinck et al., *Cold Spring Harb Perspect Biol* 8:a022103, 2016). Nonetheless, they share the same property as TβRII in that they bind only by contacting residues from a single GF monomer and not both monomers as has been shown or is predicted for all type I receptors of the family (Hinck et al., *Cold Spring Harb Perspect Biol* 8:a022103, 2016). This, together with the structures reported here that show that it is possible to remove α3 without affecting the overall structure of the monomer (FIGS. 2B-2D and FIGS. 5B-5E), suggests that it might be possible to generate monomers of other GFs of the family lacking the heel helix that function as inhibitors. These types of inhibitors have numerous potential applications, ranging from research tools for probing roles of specific ligands in vivo to clinically useful inhibitors for treating disease, which are driven by hyperactive signaling by other ligands of the family, such as cancer cachexia by activin (Coerver et al., *Mol Endocrinol* 10:534-543, 1996).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A recombinant human transforming growth factor (TGF)-β monomer, comprising:
   (i) a recombinant human TGF-β1 monomer comprising an amino acid sequence at least 95% identical to SEQ ID NO: 7, wherein the recombinant human TGF-β1 monomer comprises a cysteine to serine substitution at an amino acid residue corresponding to residue 77 of SEQ ID NO: 1; a deletion of the α3 helix corresponding to amino acid residues 52-71 of SEQ ID NO: 1; an isoleucine to arginine substitution at an amino acid residue corresponding to residue 51 of SEQ ID NO: 1; and an alanine to lysine substitution at an amino acid residue corresponding to residue 74 of SEQ ID NO: 1;
   (ii) a recombinant human TGF-β2 monomer comprising an amino acid sequence at least 95% identical to SEQ ID NO: 8 or SEQ ID NO: 10, wherein the recombinant human TGF-β2 monomer comprises a cysteine to serine substitution at an amino acid residue corresponding to residue 77 of SEQ ID NO: 2; a deletion of the α3 helix corresponding to amino acid residues 52-71 of SEQ ID NO: 2; a leucine to arginine substitution at an amino acid residue corresponding to residue 51 of SEQ ID NO: 2; and an alanine to lysine substitution at an amino acid residue corresponding to residue 74 of SEQ ID NO: 2; or
   (iii) a recombinant human TGF-β3 monomer comprising an amino acid sequence at least 95% identical to SEQ ID NO: 9, wherein the recombinant human TGF-β3 monomer comprises a cysteine to serine substitution at an amino acid residue corresponding to residue 77 of SEQ ID NO: 3; a deletion of the α3 helix corresponding to amino acid residues 52-71 of SEQ ID NO: 3; a leucine to glutamate substitution at an amino acid residue corresponding to residue 51 of SEQ ID NO: 3; and an alanine to aspartate substitution at an amino acid residue corresponding to residue 74 of SEQ ID NO: 3.

2. The recombinant human TGF-β2 monomer of claim 1, further comprising an arginine at an amino acid residue corresponding to residue 25, a lysine at an amino acid residue corresponding to residue 26, a valine at an amino acid residue corresponding to residue 89, a valine at an amino acid residue corresponding to residue 92, an arginine at an amino acid residue corresponding to residue 94, a lysine at an amino acid residue corresponding to residue 95, and a valine at an amino acid residue corresponding to residue 98 of SEQ ID NO: 2.

3. The recombinant human TGF-β monomer of claim 1, which is PEGylated or glycosylated.

4. The recombinant human TGF-β monomer of claim 1, comprising a radiotherapy agent, a cytotoxic agent for chemotherapy, a fluorescent dye, or a fluorescent protein tag.

5. The recombinant human TGF-β monomer of claim 1, which is a human recombinant TGF-β1 monomer.

6. The recombinant human TGF-β monomer of claim 1, which is a human recombinant TGF-β2 monomer.

7. The recombinant human TGF-β monomer of claim 1, which is a human recombinant TGF-β3 monomer.

8. The recombinant human TGF-β1 monomer of claim 1, further comprising an alanine to serine substitution at an amino acid residue corresponding to residue 75 of SEQ ID NO: 1.

9. The recombinant human TGF-β1 monomer of claim 1, comprising an amino acid sequence at least 98% identical to SEQ ID NO: 7.

10. The recombinant human TGF-β2 monomer of claim 1, comprising an amino acid sequence at least 98% identical to SEQ ID NO: 8.

11. The recombinant human TGF-β2 monomer of claim 1, comprising an amino acid sequence at least 98% identical to SEQ ID NO: 10.

12. The recombinant human TGF-β3 monomer of claim 1, further comprising an alanine to glutamate substitution at an amino acid residue corresponding to residue 72 of SEQ ID NO: 3.

13. The recombinant human TGF-β3 monomer of claim 1, comprising an amino acid sequence at least 98% identical to SEQ ID NO: 9.

14. The recombinant human TGF-β monomer of claim 1, which is hyper-glycosylated.

15. The recombinant human TGF-β monomer of claim 1, comprising a drug or an imaging agent.

16. A fusion protein comprising the recombinant human TGF-β monomer of claim 1 and a heterologous protein.

17. The fusion protein of claim 16, wherein the heterologous protein comprises a protein tag, an Fc domain, albumin, an albumin-binding polypeptide, an antibody, or antigen binding fragment of an antibody.

18. A composition comprising the recombinant human TGF-β monomer of claim 1, and a pharmaceutically acceptable carrier, diluent, or excipient.

19. A method of inhibiting TGF-β signaling in a cell, comprising contacting the cell with a recombinant human TGF-β monomer, wherein the amino acid sequence of the recombinant human TGF-β monomer consists of SEQ ID NO: 7, SEQ ID NO: 8, SEQ ID NO: 9, or SEQ ID NO: 10.

* * * * *

SEQUENCE LISTING

<160> NUMBER OF SEQ ID NOS: 11

<210> SEQ ID NO 1
<211> LENGTH: 112
<212> TYPE: PRT
<213> ORGANISM: Homo sapiens

<400> SEQUENCE: 1

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 2
<211> LENGTH: 112
<212> TYPE: PRT
<213> ORGANISM: Homo sapiens

<400> SEQUENCE: 2

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Lys Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

```
Lys Ile Glu Gln Leu Ser Asn Met Ile Val Lys Ser Cys Lys Cys Ser
            100                 105                 110
```

<210> SEQ ID NO 3
<211> LENGTH: 112
<212> TYPE: PRT
<213> ORGANISM: Homo sapiens

<400> SEQUENCE: 3

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110
```

<210> SEQ ID NO 4
<211> LENGTH: 129
<212> TYPE: PRT
<213> ORGANISM: Artificial Sequence
<220> FEATURE:
<223> OTHER INFORMATION: Synthetic polypeptide

<400> SEQUENCE: 4

```
Gly Leu Asn Asp Ile Phe Glu Ala Gln Lys Ile Glu Trp His Glu Glu
1               5                   10                  15

Phe Ala Leu Asp Thr Asn Tyr Cys Phe Arg Asn Leu Glu Glu Asn Cys
            20                  25                  30

Cys Val Arg Pro Leu Tyr Ile Asp Phe Arg Gln Asp Leu Gly Trp Lys
        35                  40                  45

Trp Val His Glu Pro Lys Gly Tyr Tyr Ala Asn Phe Cys Ser Gly Pro
    50                  55                  60

Cys Pro Tyr Leu Arg Ser Ala Asp Thr Thr His Ser Thr Val Leu Gly
65                  70                  75                  80

Leu Tyr Asn Thr Leu Asn Pro Glu Ala Ser Ala Ser Pro Cys Cys Val
                85                  90                  95

Pro Gln Asp Leu Glu Pro Leu Thr Ile Leu Tyr Tyr Val Gly Arg Thr
            100                 105                 110

Pro Lys Val Glu Gln Leu Ser Asn Met Val Val Lys Ser Cys Lys Cys
        115                 120                 125

Ser
```

<210> SEQ ID NO 5
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 5

```
Ala Leu Asp Ala Ala Tyr Cys Phe Arg Asn Val Gln Asp Asn Cys Cys
```

```
                1               5                  10                  15
Leu Arg Pro Leu Tyr Ile Asp Phe Lys Arg Asp Leu Gly Trp Lys Trp
                20                  25                  30

Ile His Glu Pro Lys Gly Tyr Asn Ala Asn Phe Cys Ala Gly Ala Cys
            35                  40                  45

Pro Tyr Leu Trp Ser Ser Asp Thr Gln His Ser Lys Val Leu Ser Leu
        50                  55                  60

Tyr Asn Thr Ile Asn Pro Glu Ala Ser Ala Ser Pro Ser Cys Val Ser
 65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
                100                 105                 110

<210> SEQ ID NO 6
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 6

Ala Leu Asp Thr Asn Tyr Cys Phe Arg Asn Leu Glu Glu Asn Cys Cys
 1               5                  10                  15

Val Arg Pro Leu Tyr Ile Asp Phe Arg Gln Asp Leu Gly Trp Lys Trp
                20                  25                  30

Val His Glu Pro Lys Gly Tyr Tyr Ala Asn Phe Cys Ser Gly Pro Cys
            35                  40                  45

Pro Tyr Leu Arg Ser Ala Asp Thr Thr His Ser Thr Val Leu Gly Leu
        50                  55                  60

Tyr Asn Thr Leu Asn Pro Glu Ala Ser Ala Ser Pro Ser Cys Val Pro
 65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
                100                 105                 110

<210> SEQ ID NO 7
<211> LENGTH: 92
<212> TYPE: PRT
<213> ORGANISM: Artificial Sequence
<220> FEATURE:
<223> OTHER INFORMATION: Synthetic polypeptide

<400> SEQUENCE: 7

Ala Leu Asp Thr Asn Tyr Cys Phe Ser Ser Thr Glu Lys Asn Cys Cys
 1               5                  10                  15

Val Arg Gln Leu Tyr Ile Asp Phe Arg Lys Asp Leu Gly Trp Lys Trp
                20                  25                  30

Ile His Glu Pro Lys Gly Tyr His Ala Asn Phe Cys Leu Gly Pro Cys
            35                  40                  45

Pro Tyr Arg Ala Ser Lys Ser Pro Ser Cys Val Pro Gln Ala Leu Glu
        50                  55                  60

Pro Leu Pro Ile Val Tyr Tyr Val Gly Arg Lys Pro Lys Val Glu Gln
 65                  70                  75                  80

Leu Ser Asn Met Ile Val Arg Ser Cys Lys Cys Ser
                85                  90
```

<210> SEQ ID NO 8
<211> LENGTH: 92
<212> TYPE: PRT
<213> ORGANISM: Artificial Sequence
<220> FEATURE:
<223> OTHER INFORMATION: Synthetic polypeptide

<400> SEQUENCE: 8

```
Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Arg Ala Ser Lys Ser Pro Ser Cys Val Ser Gln Asp Leu Glu
    50                  55                  60

Pro Leu Thr Ile Leu Tyr Tyr Ile Gly Lys Thr Pro Lys Ile Glu Gln
65                  70                  75                  80

Leu Ser Asn Met Ile Val Lys Ser Cys Lys Cys Ser
                85                  90
```

<210> SEQ ID NO 9
<211> LENGTH: 92
<212> TYPE: PRT
<213> ORGANISM: Artificial Sequence
<220> FEATURE:
<223> OTHER INFORMATION: Synthetic polypeptide

<400> SEQUENCE: 9

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Glu Glu Ser Asp Ser Pro Ser Cys Val Pro Gln Asp Leu Glu
    50                  55                  60

Pro Leu Thr Ile Leu Tyr Tyr Val Gly Arg Thr Pro Lys Val Glu Gln
65                  70                  75                  80

Leu Ser Asn Met Val Val Lys Ser Cys Lys Cys Ser
                85                  90
```

<210> SEQ ID NO 10
<211> LENGTH: 92
<212> TYPE: PRT
<213> ORGANISM: Artificial Sequence
<220> FEATURE:
<223> OTHER INFORMATION: Synthetic polypeptide

<400> SEQUENCE: 10

```
Ala Leu Asp Ala Ala Tyr Cys Phe Arg Asn Val Gln Asp Asn Cys Cys
1               5                   10                  15

Leu Arg Pro Leu Tyr Ile Asp Phe Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Arg Ala Ser Lys Ser Pro Ser Cys Val Ser Gln Asp Leu Glu
    50                  55                  60

Pro Leu Thr Ile Val Tyr Tyr Val Gly Arg Lys Pro Lys Val Glu Gln
```

```
65                  70                  75                  80
Leu Ser Asn Met Ile Val Lys Ser Cys Lys Cys Ser
                85                  90

<210> SEQ ID NO 11
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 11

Gly Leu Asn Asp Ile Phe Glu Ala Gln Lys Ile Glu Trp His Glu Glu
1               5                   10                  15

Phe Ala Leu Asp Ala Ala Tyr Cys Phe Arg Asn Val Gln Asp Asn Cys
                20                  25                  30

Cys Leu Arg Pro Leu Tyr Ile Asp Phe Arg Lys Asp Leu Gly Trp Lys
            35                  40                  45

Trp Ile His Glu Pro Lys Gly Tyr Asn Ala Asn Phe Cys Ala Gly Ala
        50                  55                  60

Cys Pro Tyr Arg Ala Ser Lys Ser Pro Ser Cys Val Ser Gln Asp Leu
65                  70                  75                  80

Glu Pro Leu Thr Ile Val Tyr Tyr Val Gly Arg Lys Pro Lys Val Glu
                85                  90                  95

Gln Leu Ser Asn Met Ile Val Lys Ser Cys Lys Cys Ser
                100                 105
```